(12) United States Patent
Knuckey et al.

(10) Patent No.: US 9,136,554 B2
(45) Date of Patent: Sep. 15, 2015

(54) FUEL CELLS

(75) Inventors: Kathryn Knuckey, Ormskirk (GB); Andrew Creeth, Chester (GB)

(73) Assignee: ACAL ENERGY LIMITED, Runcorn, Cheshire (GB)

(*) Notice: Subject to any disclaimer, the term of this patent is extended or adjusted under 35 U.S.C. 154(b) by 1390 days.

(21) Appl. No.: 12/374,371

(22) PCT Filed: Jul. 19, 2007

(86) PCT No.: PCT/GB2007/050421
§ 371 (c)(1),
(2), (4) Date: Jan. 11, 2010

(87) PCT Pub. No.: WO2008/009993
PCT Pub. Date: Jan. 24, 2008

(65) Prior Publication Data
US 2010/0112388 A1 May 6, 2010

(30) Foreign Application Priority Data

Jul. 19, 2006 (GB) .................................. 0614337.4

(51) Int. Cl.
*H01M 8/20* (2006.01)
*C07D 213/61* (2006.01)
(Continued)

(52) U.S. Cl.
CPC ............... *H01M 8/20* (2013.01); *C07D 213/61* (2013.01); *H01M 4/9041* (2013.01);
(Continued)

(58) Field of Classification Search
CPC ................................. H01M 8/18; H01M 8/188
USPC ............................. 429/99, 500, 502, 504, 505
See application file for complete search history.

(56) References Cited

U.S. PATENT DOCUMENTS 3,152,013 A   10/1964   Juda
3,279,949 A   10/1966   Schaefer et al.
(Continued)

FOREIGN PATENT DOCUMENTS

EP   0 043 647   1/1982
EP   0 228 168   11/1986
(Continued)

OTHER PUBLICATIONS

V. Neburchilov, J. Martin, H. Wang, J. Zhang, "A Review of Polymer Electrolyte Membranes for Direct Methanol Fuel Cells," Journal of Power Sources, 2007, vol. 159, pp. 221-238.

(Continued)

*Primary Examiner* — Ula C Ruddock
*Assistant Examiner* — Thomas Parsons
(74) *Attorney, Agent, or Firm* — Knobbe Martens Olson & Bear LLP

(57) ABSTRACT

This invention provides a redox fuel cell comprising an anode and a cathode separated by an ion selective polymer electrolyte membrane; means for supplying a fuel to the anode region of the cell; means for supplying an oxidant to the cathode region of the cell; means for providing an electrical circuit between the anode and the cathode; a non-volatile catholyte solution flowing in fluid communication with the cathode, the catholyte solution comprising a redox mediator which is at least partially reduced at the cathode in operation of the cell, and at least partially regenerated by, optionally indirect, reaction with the oxidant after such reduction at the cathode, and a transition metal complex of a multidentate N-donor ligand as a redox catalyst catalyzing the regeneration of the mediator.

32 Claims, 4 Drawing Sheets

(51) Int. Cl.
H01M 4/90 (2006.01)
H01M 8/10 (2006.01)
H01M 4/86 (2006.01)
H01M 8/06 (2006.01)

(52) U.S. Cl.
CPC ......... *H01M 8/1053* (2013.01); *H01M 4/8605* (2013.01); *H01M 8/0618* (2013.01); *Y02E 60/521* (2013.01); *Y02E 60/528* (2013.01)

(56) References Cited

U.S. PATENT DOCUMENTS

| | | | |
|---|---|---|---|
| 3,294,588 | A | 12/1966 | Beltzer et al. |
| 3,360,401 | A | 12/1967 | Grasselli et al. |
| 3,540,933 | A | 11/1970 | Boeke |
| 3,607,420 | A | 9/1971 | Cutler |
| 4,048,383 | A | 9/1977 | Clifford |
| 4,396,687 | A | 8/1983 | Kummer et al. |
| 5,250,158 | A | 10/1993 | Kaneko et al. |
| 5,298,343 | A | 3/1994 | Savadogo et al. |
| 5,384,019 | A * | 1/1995 | Keating et al. ............. 204/252 |
| 5,660,940 | A | 8/1997 | Ragnar et al. |
| 5,683,829 | A | 11/1997 | Sarangapani |
| 5,958,616 | A | 9/1999 | Salinas et al. |
| 6,054,580 | A | 4/2000 | Collins et al. |
| 6,270,649 | B1 | 8/2001 | Zeikus et al. |
| 2001/0028977 | A1 | 10/2001 | Kazacos et al. |
| 2003/0152823 | A1 | 8/2003 | Heller |
| 2004/0028203 | A1 | 2/2004 | Wurster et al. |
| 2004/0028992 | A1 | 2/2004 | Jaouen |
| 2004/0137297 | A1 | 7/2004 | Matsuoka et al. |
| 2005/0074653 | A1 | 4/2005 | Broman |
| 2005/0112055 | A1 | 5/2005 | Shannon et al. |
| 2005/0158618 | A1 | 7/2005 | Liberatore et al. |
| 2005/0244707 | A1 | 11/2005 | Skyllas-Kazacos et al. |
| 2006/0012637 | A1 | 1/2006 | Furukawa et al. |
| 2006/0024539 | A1 | 2/2006 | Dumesic |
| 2006/0088750 | A1 | 4/2006 | Nobuta et al. |
| 2006/0134493 | A1 | 6/2006 | Yoshida et al. |
| 2006/0216565 | A1 | 9/2006 | Cooray et al. |
| 2007/0078052 | A1 | 4/2007 | Grinberg et al. |
| 2007/0122689 | A1 | 5/2007 | Kubo et al. |
| 2007/0131546 | A1 | 6/2007 | Nomoto et al. |
| 2008/0274385 | A1 | 11/2008 | Creeth |
| 2009/0308752 | A1 | 12/2009 | Evans et al. |
| 2009/0317668 | A1 | 12/2009 | Creeth et al. |
| 2009/0325002 | A1 | 12/2009 | Creeth et al. |
| 2010/0112393 | A1 | 5/2010 | Creeth et al. |
| 2010/0297522 | A1 | 11/2010 | Creeth et al. |
| 2011/0014532 | A1 | 1/2011 | Knuckey et al. |
| 2011/0027671 | A1 | 2/2011 | Knuckey et al. |
| 2011/0039170 | A1 | 2/2011 | Creeth et al. |
| 2011/0091746 | A1 | 4/2011 | Knuckey et al. |

FOREIGN PATENT DOCUMENTS

| | | |
|---|---|---|
| EP | 0 517 217 | 12/1992 |
| EP | 0 595 688 | 10/1993 |
| EP | 0 592 988 | 4/1994 |
| EP | 0 790 658 | 8/1997 |
| EP | 0 878 850 | 5/1998 |
| EP | 1 143 546 | 10/2001 |
| GB | 1 176 632 | 1/1970 |
| GB | 1 176 633 | 1/1970 |
| GB | 2 400 974 | 10/2004 |
| GB | 0505087.7 | 3/2005 |
| GB | 2 424 118 | 3/2006 |
| GB | 0605878.8 | 3/2006 |
| GB | 0608079.0 | 4/2006 |
| GB | 0614337.4 | 7/2006 |
| GB | 0614338.2 | 7/2006 |
| GB | 0718349.4 | 9/2007 |
| GB | 0718577.0 | 9/2007 |
| GB | 2 440 434 | 1/2008 |
| GB | 2 440 435 | 1/2008 |
| GB | 0801195.9 | 1/2008 |
| GB | 0801198.3 | 1/2008 |
| GB | 0801199.1 | 1/2008 |
| GB | 0907795.9 | 5/2009 |
| GB | 0913638.3 | 8/2009 |
| GB | 2 440 489 | 10/2009 |
| JP | 56 042970 | 4/1981 |
| JP | 61 054163 | 3/1986 |
| JP | 62 015770 | 1/1987 |
| JP | 05 295578 | 11/1993 |
| JP | 11-288727 | 10/1999 |
| JP | 2004 319292 | 11/2004 |
| RU | 2004129396 | 3/2006 |
| WO | WO 91/13681 | 9/1991 |
| WO | WO 96/31912 | 10/1996 |
| WO | WO 00/12667 | 3/2000 |
| WO | WO 00/22688 | 4/2000 |
| WO | WO 00/29537 | 5/2000 |
| WO | WO 01/73881 | 10/2001 |
| WO | WO 03/083967 | 10/2003 |
| WO | WO 2005/112055 | 11/2005 |
| WO | WO 2006/012637 | 2/2006 |
| WO | WO 2006/057387 | 6/2006 |
| WO | WO 2006/097438 | 9/2006 |
| WO | WO 2006/121191 | 11/2006 |
| WO | WO 2007/101284 | 9/2007 |
| WO | WO 2007/110663 | 10/2007 |
| WO | WO 2007/122431 | 11/2007 |
| WO | WO 2008/009992 | 1/2008 |
| WO | WO 2008/009993 | 1/2008 |
| WO | WO 2009/037513 | 3/2009 |
| WO | WO 2009/040577 | 4/2009 |
| WO | WO 2009/093080 | 7/2009 |
| WO | WO 2009/093081 | 7/2009 |
| WO | WO 2009/093082 | 7/2009 |
| WO | WO 2010/128333 | 11/2010 |
| WO | WO 2011/015875 | 2/2011 |

OTHER PUBLICATIONS

J.G. Roelfes, "Models for Non-Heme Iron Containing Oxidation Enzymes," Jun. 4, 1972, pp. 1-154.
International Search Report for Application No. PCT/GB2007/050151, Oct. 1, 2007, pp. 5.
International Search Report with Written Opinion for Application No. PCT/GB2007/050420, Jan. 14, 2008, pp. 16.
Preliminary Search Report for PCT/GB2006/060640, Sep. 27, 2007, pp. 9.
Preliminary Search Report for PCT/GB2007/050151, Sep. 30, 2008, pp. 10.
Alley et al., "Synthesi and Characterization of ferrocenyl-phosphonic and -arsonic acids", J. Organomet. Chem., 2001, vol. 637-639, pp. 216-229.
Bernal et al., "Iron(II) Complexes of Polydentate Aminopyridyl Ligands and an Exchangeable Sixth Ligand; Reactions with peroxides . . . "-, J. Chem Soc. Trans., Dalton. Trans. 1995, pp. 3667-3675.
Chang et al., "Synthesis and Characterization of Bis(d-2-pyridylmethanamine)ruthenium(II)", Inorg. Chem., 2003, vol. 43, pp. 1735-1742.
Dillon et al., "International Activities in DMFC R&D: status of technologies and potential applications", J. Power Sources, 2004, vol. 127, pp. 112-126.
Harris et al., "Chelating Tendencies of Pyridyl-Containing Polyamines and Oxygenation of the Cobaltous Complexes", Inorg. Chem., 1978, vol. 17, pp. 889-894.
Heinzel et al., "A review of the state-of-the-art of the methanol crossover in direct methanol fuel cells", J. Power Sources, 1999, vol. 84, pp. 70-74.
Hogarth et al., "Catalysis for Low Temperature Fuel Cells", Platinum Metal Reviews, 2002, vol. 46, pp. 146-164.
Klopstra et al., "Non-heme iron catalyts for the benzylic oxidation: a parallel ligand screening approach", Tet. Lett., 2003, vol. 44, pp. 4581-4584.
Knox et al., "Ferrocene Derivatives. Part VII. Some Sulphur derivatives", J. Chem. Soc., 1958, vol. 682.

(56) References Cited

OTHER PUBLICATIONS

Limoges et al., "Electrocatalyst materials for fuel cells based on the polyoxometalates [PMo(12−n)Vn040]<(3+n)->(n=0−3)", Electrochimica Acta, Elsevier Scient Publishers, Jan. 15, 2005, vol. 50, Issue 5, pp. 1169,1170,1176-1179 , Barking, GB.

Lubben et al., "Nonheme Iron Centers in Oxygen Activation: Characterization of an Iron(III) Hydroperoxide Intermediate", Angew, Chem. Int. Ed. Engl., 1995, vol. 34, pp. 1512-1514.

Reger et al., "Synthesis and structural characterization of the bitopic ferrocene-based tris(pyrazolyl)methana ligand Fe[C5H4CH2OCH2C(pz)3]2 (pz=pyrazolyl ring)", J. Chem Crystallography, 2005, vol. 35, pp. 217-225.

Sato et al., "Convenient Synthesis of N,N,N',N'Tetrakis(2-pyridylmethyi)-a,w-alkanediamines Using a Phase-Transfer Catalyst", Synthesis, 1992, pp. 539-540.

Tamura et al., "Superoxide Dismutase Activity of Iron(III) TPEN complex and its Derivatives", Chem. Pharm. Bull, 2000, vol. 48, pp. 1514-1518.

Van Den Heuval et al., "Synthesis of a Non-Heme Template for Attaching Four Peptides: An Approach to Artificial Iron(II)-Containing Peroxides", J. Organ. Chem., 2004, vol. 69, pp. 250-262.

* cited by examiner

FUEL CELLS

CROSS-REFERENCE TO RELATED APPLICATIONS

This Application is the US National Phase under 35 U.S.C. §371 of International Application No. PCT/GB2007/050421, filed Jul. 19, 2007, which was published in English as International Publication No. WO 2008/09993 on Jan. 24, 2008, and claims the benefit of GB 0614337.4, filed Jul. 19, 2006.

BACKGROUND

1. Field

The present invention relates to fuel cells, in particular to indirect or redox fuel cells which have applications as power sources for: portable products such as portable electronics products; for transport vehicles such as automobiles, both main and auxiliary; auxiliary power for caravans and other recreational vehicles, boats etc; stationary uses such as uninterruptible power for hospitals computers etc and combined heat and power for homes and businesses. The invention also relates to the use of certain catalysts for use in such fuel cells.

2. Description of the Related Art

Fuel cells have been known for portable applications such as automotive and portable electronics technology for very many years, although it is only in recent years that fuel cells have become of serious practical consideration. In its simplest form, a fuel cell is an electrochemical energy conversion device that converts fuel and oxidant into reaction product(s), producing electricity and heat in the process. In one example of such a cell, hydrogen is used as fuel, and air or oxygen as oxidant and the product of the reaction is water. The gases are fed respectively into catalysing, diffusion-type electrodes separated by a solid or liquid electrolyte which carries electrically charged particles between the two electrodes. In an indirect or redox fuel cell, the oxidant (and/or fuel in some cases) is not reacted directly at the electrode but instead reacts with the reduced form (oxidized form for fuel) of a redox couple to oxidise it, and this oxidised species is fed to the cathode (anode for fuel).

There are several types of fuel cell characterised by their different electrolytes. The liquid electrolyte alkali electrolyte fuel cells have inherent disadvantages in that the electrolyte dissolves $CO_2$ and needs to be replaced periodically. Polymer electrolyte or PEM-type cells with proton-conducting solid cell membranes are acidic and avoid this problem. However, it has proved difficult in practice to attain power outputs from such systems approaching the theoretical maximum level, due to the relatively poor electrocatalysis of the oxygen reduction reaction. In addition expensive noble metal electrocatalysts are often used.

Many current fuel cell technologies employ cathodes where oxygen gas is flowed directly to the electrode where it then reacts with a catalyst to produce water. In many cases the catalyst employed is platinum, a precious metal. Not only does this increase the costs of the overall fuel cell, but the inefficiency of the reaction leads to a loss in available power.

U.S. Pat. No. 3,152,013 discloses a gaseous fuel cell comprising a cation-selective permeable membrane, a gas permeable catalytic electrode and a second electrode, with the membrane being positioned between the electrodes and in electrical contact only with the gas permeable electrode. An aqueous catholyte is provided in contact with the second electrode and the membrane, the catholyte including an oxidant couple therein. Means are provided for supplying a fuel gas to the permeable electrode, and for supplying a gaseous oxidant to the catholyte for oxidising reduced oxidant material. The preferred catholyte and redox couple is HBr/KBr/$Br_2$. Nitrogen oxide is disclosed as a preferred catalyst for oxygen reduction, but with the consequence that pure oxygen was required as oxidant, the use of air as oxidant requiring the venting of noxious nitrogen oxide species.

An acknowledged problem concerning electrochemical fuel cells is that the theoretical potential of a given electrode reaction under defined conditions can be calculated but never completely attained. Imperfections in the system inevitably result in a loss of potential to some level below the theoretical potential attainable from any given reaction. Previous attempts to reduce such imperfections include the selection of catholyte additives which undergo oxidation-reduction reactions in the catholyte solution. For example, U.S. Pat. No. 3,294,588 discloses the use of quinones and dyes in this capacity. Another redox couple which has been tried is the vanadate/vanadyl couple, as disclosed in U.S. Pat. No. 3,279,949.

According to U.S. Pat. No. 3,540,933, certain advantages could be realised in electrochemical fuel cells by using the same electrolyte solution for both catholyte and anolyte. This document discloses the use of a liquid electrolyte containing more than two redox couples therein, with equilibrium potentials not more than 0.8 V apart from any other redox couple in the electrolyte.

The matching of the redox potentials of different redox couples in the electrolyte solution is also considered in U.S. Pat. No. 3,360,401, which concerns the use of an intermediate electron transfer species to increase the rate of flow of electrical energy from a fuel cell. The use of platinum coated electrodes is also disclosed.

Several types of proton exchange membrane fuel cells exist. For example, in U.S. Pat. No. 4,396,687 a fuel cell is disclosed which comprises regenerable anolyte and catholyte solutions. The anolyte solution is one which is reduced from an oxidised state to a reduced state by exposure of the anolyte solution to hydrogen. According to U.S. Pat. No. 4,396,687, preferred anolyte solutions are tungstosilicic acid ($H_4SiW_{12}O_{40}$) or tungstophosphoric acid ($H_3PW_{12}O_{40}$) in the presence of a catalyst.

The preferred catholyte solution of U.S. Pat. No. 4,396,687 is one which is re-oxidised from a reduced state to an oxidized state by direct exposure of the catholyte solution to oxygen. The catholyte of U.S. Pat. No. 4,396,687 includes a mediator component comprising a solution of $VOSO_4$. The mediator functions as an electron sink which is reduced from an oxidation state of $V^{(v)}$ to $V^{(IV)}$. The catholyte also includes a catalyst for regenerating the mediator to its oxidised state, $(VO_2)_2SO_4$. The catalyst present in the catholyte of U.S. Pat. No. 4,396,687 is a polyoxometallate (POM) solution, namely $H_5PMo_{10}V_2O_{40}$.

A significant amount of investigation into the interaction of certain N-donor complexes with oxidants such as hydrogen peroxide or peracids has been reported in the general literature and elsewhere.

WO-A-0012667 describes the use of N-donor complexes as transition metal bleach catalysts which can catalyse the oxidation of stains by air or dioxygen in aqueous solution.

WO0029537 describes the use of transition metal complexes containing cross-bridged macropolycyclic N-donor ligands as bleach catalysts which operate in detergent compositions which are substantially free of any organic or inorganic peroxygen compounds.

A thesis from the University of Groningen entitled 'Models for non-heme iron containing oxidation enzymes' by J. G.

Roelfes mentions that Fe(N4Py) type complexes are capable of oxygen activation as demonstrated in DNA cleavage experiments.

M. Klopstra, R. Hage, R. M. Kellogg and B. L Fering a, *Tet. Lett.*, 2003, 44, 4581: discusses benzylic oxidation by catalysts such as Fe(N4Py) using $O_2$ as the oxidant. An autoxidation mechanism is proposed where Fe catalyst reacts with 1-phentlethylhydroperoxide.

U.S. Pat. No. 5,298,343 relates to polycomponent electrocatalysts suitable for use at the cathode of electrochemical and fuel cells.

US-A-2005/0112055 discloses a catalyst comprising a di-ruthenium-substituted polyoxometallate.

Prior art fuel cells all suffer from one or more of the following disadvantages:

They are inefficient; they are expensive and/or expensive to assemble; they use expensive and/or environmentally unfriendly materials; they yield inadequate and/or insufficiently maintainable current densities and/or cell potentials; they are too large in their construction; they operate at too high a temperature; they produce unwanted by-products and/or pollutants and/or noxious materials; they have not found practical, commercial utility in portable applications such as automotive and portable electronics.

SUMMARY

It is an object of the present invention to overcome or ameliorate one or more of the aforesaid disadvantages. It is a further object of the present invention to provide an improved catholyte solution for use in redox fuel cells.

Accordingly, the present invention provides a redox fuel cell comprising an anode and a cathode separated by an ion selective polymer electrolyte membrane; means for supplying a fuel to the anode region of the cell; means for supplying an oxidant to the cathode region of the cell; means for providing an electrical circuit between the anode and the cathode; a catholyte solution comprising at least one non-volatile catholyte component flowing in fluid communication with the cathode, the catholyte solution comprising a redox mediator which is at least partially reduced at the cathode in operation of the cell, and at least partially regenerated by, optionally indirect, reaction with the oxidant after such reduction at the cathode, the catholyte solution comprising a complexed multidentate N-donor ligand as said redox mediator and/or as a redox catalyst catalysing the regeneration of the said mediator.

The catholyte may comprise the complexed multidentate N-donor ligand (the "ligand complex") as said redox mediator, and as said redox catalyst. Alternatively, the catholyte solution may comprise one or more alternative redox mediators, and the ligand complex as redox catalyst for the said mediator(s). Alternatively, the catholyte solution may comprise the ligand complex as redox mediator and one or more alternative redox catalysts for the ligand complex mediator. In other words the ligand complex can function alternatively as redox mediator and/or as redox catalyst in the catholyte solution, with or without one or more secondary redox mediator(s) and/or redox catalyst(s).

Thus, in a first system in accordance with the invention, the ligand complex functions as a redox catalyst (referred to below as "Cat") and is at least partially oxidised in the cathode region of the cell in operation thereof, and then reduced back to its original state at the electrode in regenerative redox cycle with the redox mediator (referred to below as "Med") in accordance with Scheme I:

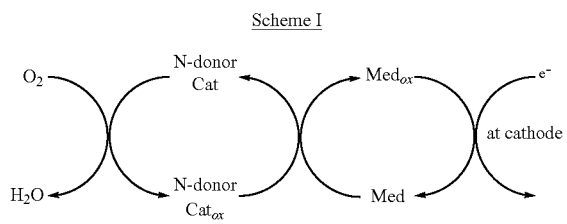

Scheme I

In a second system in accordance with the invention, an alternative redox catalyst (referred to below as "Cat") and is at least partially oxidised in the cathode region of the cell in operation thereof, and then reduced back to its original state at the electrode in regenerative redox cycle with the ligand complex redox mediator (referred to below as "Med") in accordance with Scheme II:

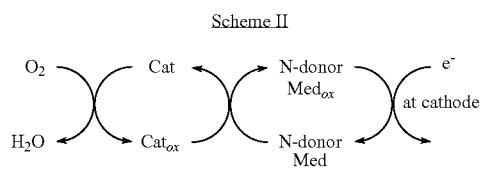

Scheme II

In a third system in accordance with the invention, the ligand complex functions as both redox catalyst (referred to below as "Cat") and as redox mediator (referred to below as "Med") in accordance with Scheme III:

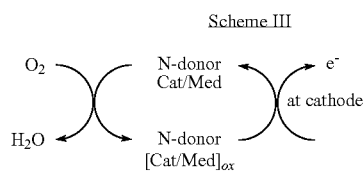

Scheme III

Accordingly, in operation of the fuel cell of the invention the oxidant (i.e. oxygen or any other suitable oxidant) is reduced in the catholyte solution by the redox catalyst. Preferably, the resulting oxidised redox catalyst is effective at least partially to oxidise the mediator to regenerate the mediator after its reduction at the cathode.

For fuel cell operation, oxygen reduction must be efficiently catalysed. Conventional technologies tend to employ heterogeneous catalysts for oxygen reduction, where a catalyst such as platinum is deposited at the electrode and termed an electrocatalyst. The present system instead (or as well) uses homogeneous catalysis, e.g. a water-soluble catalyst for oxygen reduction.

Homogeneous catalyst systems have been described before in connection with fuel cells. One such is described in our own co-pending United Kingdom patent application no. 0605878.8, in which a polyoxometallate (POM) system is used as a catalyst. However, in certain types of fuel cell it may be desirable not to have such a high concentration of metal centres in the catalyst as are present in the polyoxometallate system:

It would therefore be advantageous to provide a catalytic system which is soluble in the catholyte solution (e.g. in aqueous solution when the catholyte solution is aqueous) but offers a similar catalytic rate of oxygen reduction at lower concentrations of catalyst, and/or operates at a higher potential. Additionally, a catalyst which can interact with a range of different mediators and/or additional catalysts, and a mediator which can interact with a range of different catalysts and/or additional mediators without precipitation could allow access to a versatile system capable of achieving increased current densities.

Also provided in accordance with the invention is a catholyte solution for use in such a redox fuel cell, the catholyte solution comprising at least one transition metal complex of a multidentate N-donor ligand as redox mediator and/or as redox catalyst.

Thus, we have found that complexed multidentate N-donor ligands in particular can be effective redox catalysts and/or redox mediators in fuel cell operation. Surprisingly, rates of catalysis on a molar basis similar to the POM system described in our co-pending United Kingdom patent application no. 0605878.8 are achievable by employing a lower relative concentration of metal centres.

The fuel cell of the invention preferably comprises at least one such complexed ligand in the catholyte solution. The N-donor ligands may generally be coordinated with any suitable metal or metals, for example suitable transition metals. Specific examples of suitable transition metal ions which can form complexes include manganese (II-V), iron (I-IV), copper (I-III), cobalt (I-III), nickel (I-III), chromium (II-VII), titanium (II-IV), tungsten (IV-VI), vanadium (II-V), and molybdenum (II-VI). More preferably the transition metal should be manganese (II-V), iron (I-IV), copper (I-III) or cobalt (I-III). The ligands themselves may contain carbon, hydrogen, oxygen, nitrogen, sulphur, halides and/or phosphorous, for example.

The N-donor ligand may be a polymeric or oligomeric species and hence contain any large number of nitrogen atoms capable of binding to a transition metal centre. The ligating species on the ligand may comprise one or more cyclic groups, one or more acyclic groups and mixtures of cyclic and acyclic groups. Cyclic groups may or may not be aromatic.

When the multidentate N-donor ligand is a non-polymeric small molecule, it can contain up to 8 nitrogen atoms capable of coordinating to a transition metal centre and may coordinate through each or any of these nitrogen atoms. Preferably, the multidentate N-donor ligand should contain between three and six nitrogen atoms capable of coordinating to a transition metal centre and may complex to transition metals via any or each of those three to six nitrogen atoms. More preferably the N-donor ligand should contain four, five or six nitrogen atoms capable of coordinating to a transition metal centre. In especially preferred embodiments, the N-donor ligand contains five or six nitrogen atoms capable of coordinating to a transition metal centre. Of these N-donor atoms, at least one, but up to five, may be contained within an optionally substituted aromatic heterocycle. More preferably the aromatic heterocycle may be an optionally substituted pyridyl or pyridylmethyl ring, which may contain any number of substituent functional groups at any position/s on the ring. Such substituent functional groups include sulphate, sulphonate, sulphonic acid, phosphate, phosphonate, phosphonic acid, carboxylate, carboxylic acid and/or halides being a selection of non-limiting examples. The remaining N-donor atoms may exist in non-aromatic cyclic or acyclic environments, including primary, secondary and/or tertiary amine sites. Other atoms contained within the N-donor ligand may include carbon, hydrogen, oxygen, sulphur, phosphorous and/or halides, some of which may additionally coordinate to the metal centre.

The or each functional group may therefore be spaced from the aromatic heterocycle by any suitable number of spacer elements, for example alkyl, alkenyl, aryl, cycloalkyl, alkaryl alkenaryl, aralkyl or aralkenyl spacer elements, in which where appropriate any hydrocarbon chain may be straight or branched.

"Alkyl" is preferably $C_{1-6}$ alkyl, for example $C_{2-6}$ alkyl, $C_{1-5}$ alkyl, $C_{2-5}$ alkyl, $C_{1-4}$ alkyl, $C_{2-4}$ alkyl, $C_{1-3}$ alkyl, $C_{2-3}$ alkyl, $C_{1-2}$ alkyl. The same $C_{number}$ ranges apply to alkenyl groups and to the alkyl or alkenyl parts of any aralkyl, aralkenyl, alkaryl or alkenaryl groups.

One example of a particularly preferred N-donor ligand structure is given below:

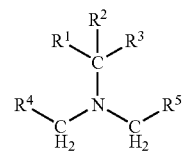

Wherein $R^1$ to $R^5$ are independently any group or atom, with from two to five, more preferably, three to five, and most preferably four of $R^1$ to $R^5$ comprising organic groups containing an N donor atom, with from one to five, more preferably three to five and most preferably four, of those N donor atoms belonging to one or more optionally substituted aromatic heterocycles. Preferably, the or each aromatic heterocycle is an optionally substituted pyridyl or pyridylmethyl ring, which may contain any number of substituent functional groups at any position/s on the ring. Such substituent functional groups include sulphate, sulphonate, sulphonic acid, phosphate, phosphonate, phosphonic acid, carboxylate, carboxylic acid and/or halides as a selection of non-limiting examples. The remaining atoms in groups $R^1$ to $R^5$ can include carbon, hydrogen, oxygen, sulphur, phosphorous and/or halides, some of which may additionally coordinate to the metal centre.

Two particularly preferred N-donor ligands of this type are N,N-bis(pyridine-2-yl-methyl)-bis(pyridine-2-yl)methylamine (N4Py) and N,N-bis(pyridine-2-yl-methyl)-1,1-bis(pyridine-2-yl)-1-aminoethane (MeN4Py):

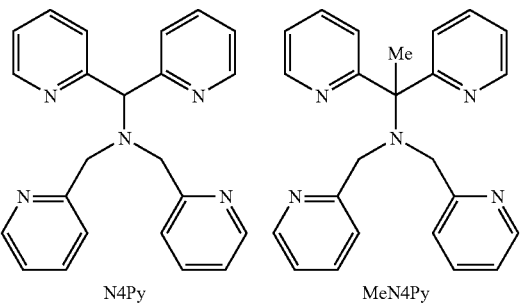

An example of another particularly preferred structure is given below:

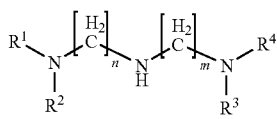

In this structure n and m may be the same or different and may be any integer from 1 to 10, more preferably n and m are independently 1 to 5, most preferably n and m are independently 1 to 3, with n=m=2 being particularly preferred. Between one and three, or more preferably one or two, but most preferably two, of $R^1$ to $R^4$ are organic group/s containing an N donor atom. In preferred embodiments, one to three of those N-donor atoms belong to an optionally substituted aromatic heterocycle. Most preferably, two of the N-donor atoms belong to optionally substituted aromatic heterocycles. The aromatic heterocycle is preferably an optionally substituted pyridyl or pyridylmethyl ring, which may contain any number of substituent functional groups at any position/s on the ring. Such substituent functional groups include sulphate, sulphonate, sulphonic acid, phosphate, phosphonate, phosphonic acid, carboxylate, carboxylic acid and/or halides as a selection of non-limiting examples. The remaining atoms in groups $R^1$ to $R^4$ can include carbon, hydrogen, oxygen, sulphur, phosphorous and/or halides, some of which may additionally coordinate to the metal centre.

A particularly preferred N-donor of this type is 1,9-bis(2-pyridyl)-2,5,8-triazanonane (pydien):

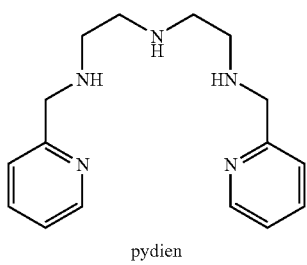 [SMILES: c1ccc(CNCCNCCNCc2ccccn2)nc1]

pydien

An example of another preferred structure is given below:

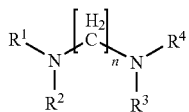

Preferably, n is any integer from 1 to 10, more preferably n is from 1 to 5, most preferably n is 1 to 3, with n=2 being particularly preferred. One to four, more preferably two to four and most preferably 3 of $R^1$ to $R^4$ are organic groups containing an N donor atom, with at least one, but up to four and more preferably three or four of those N-donor atoms belonging to an optionally substituted aromatic heterocycle. In preferred embodiments, the aromatic heterocycle is an optionally substituted pyridyl or pyridylmethyl ring, which may contain any number of substituent functional groups at any position/s on the ring. Substituent functional groups which may be incorporated in such heterocycles include, sulphate, sulphonate, sulphonic acid, phosphate, phosphonate, phosphonic acid, carboxylate, carboxylic acid and/or halides as a selection of non-limiting examples. The remaining atoms in groups $R^1$ to $R^4$ can include carbon, hydrogen, oxygen, sulphur, phosphorous and/or halides, some of which may additionally coordinate to the metal centre.

Particularly preferred N-donors of this type are N-methyl-N,N',N'-tris(2-pyridylmethyl)ethane-1,2-diamine (trilen) and N,N,N',N'-tetrakis(2-pyridylmethyl_ethane-1,2-diamine (tpen):

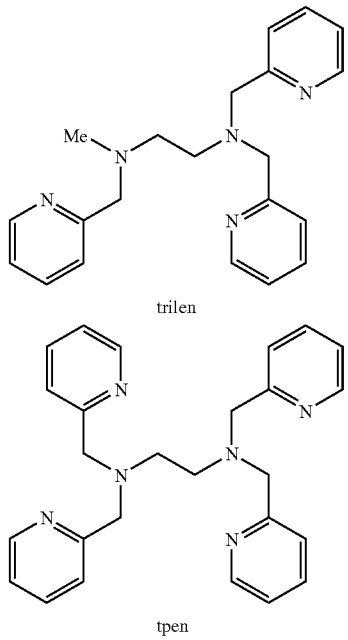

trilen tpen

It may be desirable, for example if the complete N-donor metal complex is to be used as a catalyst and/or mediator in a PEM cell comprising a cation exchange membrane, that the complex be non-ionic in its oxidized form or, preferably, anionic. In this or in any other desired case, anionic charge can be introduced by modifying the N-donor ligand with one or more anionic charge inducing groups such as carboxylate, carboxylic acid, phosphate, phosphonate or phosphonic acid groups. Stronger acid groups such as sulphonate, sulphate or sulphonic acid could also be introduced. Specific examples of preferred N-donor ligands of this sort are N-methyl-N,N',N',-tris(2-(4-sulfonato)-pyridylmethyl)ethane-1,2-diamine trisodium salt (trilen-$(SO_3Na)_3$), N-methyl-N,N',N',-tris(2-(4-sulfato)-pyridylmethyl)ethane-1,2-diamine trisodium salt (trilen-$(OSO_3Na)_3$), N-methyl-N,N',N'-tris(2-(4-sulphonic acid)pyridylmethyl)-ethane-1,2-diamine (trilen-$(SO_3H)_3$), N-methyl-N,N',N'-tris(2-(4-sulphate)-pyridylmethyl) ethane-1,2-diamine (trilen-$(OSO_3H)_3$), N-methyl-N,N',N'-tris(2-(4-methylsulfonato)-pyridylmethyl)ethane-1,2-diamine trisodium salt (trilen-$(CH_2SO_3Na)_3$); N-methyl-N,N', N',-tris(2-(4-methylsulfato)pyridylmethyl)-ethane-1,2-diamine trisodium salt (trilen-$(CH_2OSO_3Na)_3$), N-methyl-N, N',N'-tris(2-(4-methylsulphonic acid)-pyridylmethyl) ethane-1,2-diamine (trilen-$(CH_2SO_3H)_3$), N-methyl-N,N', N',-tris(2-(4-methylsulphate)-pyridyl-methyl)ethane-1,2-diamine (trilen-$(CH_2OSO_3H)_3$), N,N,N',N'-tetrakis(2-(4-sulfonato)-pyridylmethyl)ethane-1,2-diamine tetra-sodium salt (tpen-$(SO_3Na)_4$), N,N,N',N'-tetrakis(2-(4-sulfato)-pyridylmethypethane-1,2-diamine tetra-sodium salt (tpen-$(OSO_3Na)_4$), N,N,N',N'-tetrakis(2-(4-sulphonic acid)-pyridylmethyl)ethane-1,2-diamine (tpen-$(SO_3H)_4$), N,N,N',N'-tetrakis(2-(4-sulphate)-pyridylmethyl)ethane-1,2-diamine (tpen-$(OSO_3H)_4$), N,N,N',N'-tetrakis(2-(4-methylsulfonato)-pyridylmethyl)ethane-1,2-diamine tetrasodium salt (tpen-(CH$_2$SO$_3$Na)$_4$), N,N,N',N'-tetrakis(2-(4-methyl-sulfato)-pyridylmethyl)-ethane-1,2-diamine tetrasodium salt (tpen-(CH$_2$OSO$_3$Na)$_4$), N,N,N',N'-tetrakis-(2-(4-methylsulphonic acid)-pyridylmethyl)ethane-1,2-diamine (tpen-(CH$_2$SO$_3$H)$_4$) and N,N,N',N'-tetrakis(2-(4-methylsulphate)-pyridylmethyl)-ethane-1,2-diamine (tpen-(CH$_2$OSO$_3$H)$_4$):

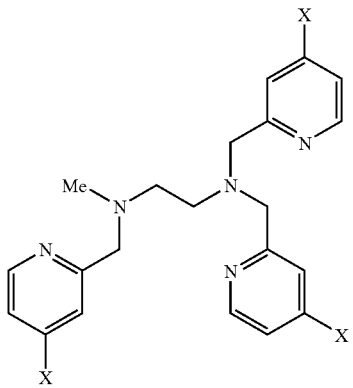

X = SO$_3$H   trilen-(SO$_3$H)$_3$
X = OSO$_3$H   trilen-(OSO$_3$H)$_3$
X = SO$_3$Na   trilen-(SO$_3$Na)$_3$
X = OSO$_3$Na   trilen-(OSO$_3$Na)$_3$

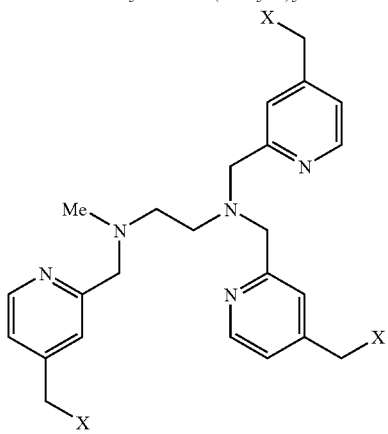

X = SO$_3$H   trilen-(CH$_2$SO$_3$H)$_3$
X = OSO$_3$H   trilen-(CH$_2$OSO$_3$H)$_3$
X = SO$_3$Na   trilen-(CH$_2$SO$_3$Na)$_3$
X = OSO$_3$Na   trilen-(CH$_2$OSO$_3$Na)$_3$

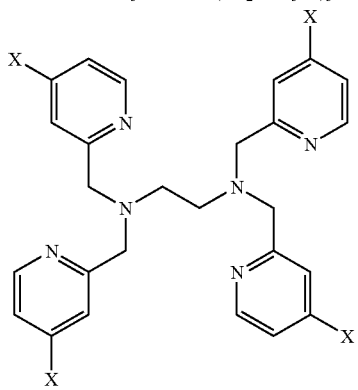

X = SO$_3$H   tpen-(SO$_3$H)$_4$
X = OSO$_3$H   tpen-(OSO$_3$H)$_4$
X = SO$_3$Na   tpen-(SO$_3$Na)$_4$
X = OSO$_3$Na   tpen-(OSO$_3$Na)$_4$ -continued

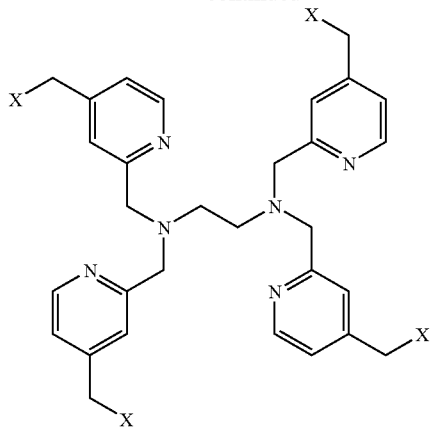

X = CH$_2$SO$_3$H   tpen-(CH$_2$SO$_3$H)$_4$
X = CH$_2$OSO$_3$H   tpen-(CH$_2$OSO$_3$H)$_4$
X = CH$_2$SO$_3$Na   tpen-(CH$_2$SO$_3$Na)$_4$
X = CH$_2$OSO$_3$Na   tpen-(CH$_2$OSO$_3$Na)$_4$ As part of the investigative work in connection with N donor ligands undertaken in relation to this invention, a novel material, namely N-methyl-N,N',N'-tris(2-(4-chloro)-pyridylmethyl)ethane-1,2-diamine (trilen-Cl$_3$), was synthesised.

According to the present invention, there is provided N-methyl-N,N',N',-tris(2-(4-chloro)-pyridylmethyl)ethane-1,2-diamine (trilen-Cl$_3$), and its use in the catholyte solution of a fuel cell in accordance with this invention.

Alternatively, when the complete N-donor metal complex is to be used as a catalyst and/or mediator in a PEM cell comprising a anion exchange membrane, it will preferably be non-ionic in its reduced form, or more preferably, cationic. Cationic charge can be introduced to the N-donor ligand by modifying it with cationic charge inducing groups such as protonated amines or quaternary amine groups.

The complete redox catalyst complex should be between four and eight coordinate, but more preferably six coordinate overall. Where the number of coordinating nitrogen atoms contained within the N-donor ligand is less than six, additional coordinating species are required. These species may be mono-, bi- and/or tridentate and may be either neutral or negatively charged. One skilled in the art will appreciate the vast array of suitable coordinating species which includes H$_2$O, OH$^-$, Cl$^-$, CH$_3$OH and CH$_3$CN as non-limiting examples.

In order to balance the charge of the transition metal catalyst, non-coordinating counter cations or anions are also present. Again, one skilled in the art will appreciate the vast array of suitable counter ions which includes ClO$_4^-$, PF$_6^-$, Cl$^-$, CN$^-$, SO$_4^{2-}$, Na$^+$ and K$^+$ as non-limiting examples.

Redox mediators and/or catalysts for use in conjunction with the N-donor ligand complex can be selected from a very large range of suitable materials, including ligated transition metal complexes and polyoxometallate species. Specific examples of suitable transition metals ions which can form such complexes include manganese (II-V), iron (I-IV), copper (I-III), cobalt (I-III), nickel (I-III), chromium (II-VII), titanium (II-IV), tungsten (IV-VI), vanadium (II-V) and molybdenum (II-VI). Ligands in such ligated transition metal complexes may be chelating such as 2,2'-bipyridine and/or 1,10-phenanthroline, or non-chelating such as chloride and/or cyanide. Complexes of such ligands (e.g. transition metal complexes) may contain solely chelating or non-chelating ligands, or a mixture of the two.

One preferred redox mediator comprises a modified ferrocene species and is disclosed in our co-pending application UK 0614338.2.

If a modified ferrocene species is to be used as a redox mediator in a PEM cell comprising a cation exchange membrane, it will preferably be non-ionic in its oxidized form or, more preferably, anionic. Anionic charge can be introduced to ferrocene by modifying it with anionic charge inducing groups such as carboxylate, carboxylic acid, phosphate, phosphonate or phosphonic acid groups. Stronger acid groups such as sulphonate, sulphate or sulphonic acid could also be introduced.

Alternatively, when the modified ferrocene species is to be used as a redox mediator in a PEM cell comprising a anion exchange membrane, it will preferably be non-ionic in its reduced form, or more preferably, cationic. Cationic charge can be introduced to ferrocene by modifying it with cationic charge inducing groups such as protonated amines or quaternary amine groups.

Thus, it can be seen that the charge of the modified ferrocene species can be easily modified. This allows it to be tailored to the particular conditions of the cell with which it is to be used. For example, it can be tailored to the potential of the catholyte redox catalyst and the pH of the catholyte.

When the redox mediator is a modified ferrocene species, it may be represented by the formula:

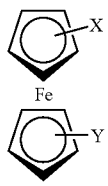

wherein:
X and Y are independently selected from hydrogen and functional groups comprising halogen, hydroxy, amino, protonated amino, imino, nitro, cyano, acyl, acyloxy, sulphate, sulphonyl, sulphinyl, alkylamino, protonated alkylamino, quaternary alkylammonium, carboxy, carboxylic acid, ester, ether, amido, sulphonate, sulphonic acid, sulfonamide, phosphonyl, phosphonic acid, alkylsulphonyl, arylsulphonyl, alkoxycarbonyl, alkylsulphinyl, arylsulphinyl, alkylthio, arylthio, alkyl, alkoxy, oxyester, oxyamido, aryl, arylamino, aryloxy, heterocycloalkyl, heteroaryl, ($C_2$-$C_5$)alkenyl, ($C_2$-$C_5$)alkynyl, azido phenylsulphonyloxy or amino acid conjugates having the formula —CO—W—OH, where W is an amino acid.

Preferably, at least one of X and Y are independently selected from hydrogen and functional groups comprising, halogen, hydroxy, amino, protonated amino, imino, acyl, sulphate, alkylamino, protonated alkylamino, quaternary alkylammonium, carboxy, carboxylic acid, ester, oxyester, alkoxy, sulphonyl, sulphinyl, alkylsulphonyl, sulphonic acid, sulphonamide, phosphonic acid, phosphonate, phosphate, amido, oxyamido or amino acid conjugates having the formula —CO—W—OH, where W is an amino acid and from alkyl, alkenyl, aryl, cycloalkyl, alkaryl alkenaryl, aralkyl, aralkenyl groups substituted with one or more of the aforesaid functional groups.

More preferably, at least one of X and Y are independently selected from hydrogen and functional groups comprising F, CHO, —$COCH_3$, —$COCH_2CH_3$, —$COCH_2CH_2COOH$, —COOH, —$(COOH)_2$, —$NH_2$, $NH_3^+$, —$N(CH_3)_2$, —$NH(CH_3)_2^+$, —$N(CH_3)_3^+$, —$H(CH_2CH_3)_2$, —$NH(CH_2CH_3)^+$, —$N(CH_2CH_3)_3^+$, —$CH_2N(CH_3)_2$, $CH_2NH(CH_3)_2^+$, —$CH_2N(CH_3)_3^+$, —OH, —$CH_2OH$, —$CH(OH)CH_3$, —$SO_3^-$, —$CH_2SO_3^-$, —$CH_2OSO_3^-$, $PO(OH)_2$, —$OPO(OH)_2$—CO-Gly-OH, —CO-Glu-OH or —CO-Asp-OH, and from alkyl, alkenyl, aryl, cycloalkyl, alkaryl alkenaryl, aralkyl, aralkenyl groups substituted with one or more of the aforesaid functional groups.

There may be any number from 1 to 5 X substituents, in which case each X substituent may be the same or different. There may be any number from 1 to 5 Y substituents, in which case each Y substituent may be the same or different. All five X groups and all five Y groups cannot concomitantly be hydrogen.

The concentration of the redox mediator in the catholyte solution is preferably at least about 0.0001M, more preferably at least about 0.005M, and most preferably at least about 0.001M.

The concentration of the redox catalyst in the catholyte solution is preferably at least about 0.0001M, more preferably at least about 0.005M, and most preferably at least about 0.001M.

In one preferred embodiment of the invention, the ion selective PEM is a cation selective membrane which is selective in favour of protons versus other cations. In this case the pH of the catholyte is preferably acidic. It preferably has a pH of below 7, more preferably below 4, even more preferably below 2 and most preferably below 1.

The cation selective polymer electrolyte membrane may be formed from any suitable material, but preferably comprises a polymeric substrate having cation exchange capability. Suitable examples include fluororesin-type ion exchange resins and non-fluororesin-type ion exchange resins. Fluororesin-type ion exchange resins include perfluorocarboxylic acid resins, perfluorosulphonic acid resins, and the like. Perfluorocarboxylic acid resins are preferred, for example "Nafion" (Du Pont Inc.), "Flemion" (Asahi Gas Ltd), "Aciplex" (Asahi Kasei Inc), and the like. Non-fluororesin-type ion exchange resins include polyvinyl alcohols, polyalkylene oxides, styrene-divinylbenzene ion exchange resins, and the like, and metal salts thereof. Preferred non-fluororesin-type ion exchange resins include polyalkylene oxide-alkali metal salt complexes. These are obtainable by polymerizing an ethylene oxide oligomer in the presence of lithium chlorate or another alkali metal salt, for example. Other examples include phenolsulphonic acid, polystyrene sulphonic, polytrifluorostyrene sulphonic, sulphonated trifluorostyrene, sulphonated copolymers based on $\alpha,\beta,\beta$ trifluorostyrene monomer, radiation-grafted membranes. Non-fluorinated membranes include sulphonated poly(phenylquinoxalines), poly (2,6 diphenyl-4-phenylene oxide), poly(arylether sulphone), poly(2,6-diphenylenol); acid-doped polybenzimidazole, sulphonated polyimides; styrene/ethylene-butadiene/styrene triblock copolymers; partially sulphonated polyarylene ether sulphone; partially sulphonated polyether ether ketone (PEEK); and polybenzyl suphonic acid siloxane (PBSS).

In another preferred embodiment of the invention, the ion selective PEM is an anionic selective membrane. Suitable examples of anionic membranes include quaternary amine derivatives of styrene cross-linked with divinyl benzene and polymerised in the presence of finely powdered polyvinyl chloride to provide strength.

In embodiments where the PEM is anion selective, the catholyte is preferably alkaline. It preferably has a pH above 7, more preferably above 8.

In some cases it may be desirable for the ion selective polymer electrolyte membrane to comprise a bi-membrane. The bimembrane if present will generally comprise a first cation selective membrane and a second anion selective membrane. In this case the bimembrane may comprise an adjacent pairing of oppositely charge selective membranes. For example the bimembrane may comprise at least two discrete membranes which may be placed side-by-side with an optional gap there between. Preferably the size of the gap, if any, is kept to a minimum in the redox cell of the invention. The use of a bi-membrane may be used in the redox fuel cell of the invention to maximise the potential of the cell, by maintaining the potential due to a pH drop between the anode and catholyte solution. Without being limited by theory, in order for this potential to be maintained in the membrane system, at some point in the system, protons must be the dominant charge transfer vehicle. A single cation-selective membrane may not achieve this to the same extent due to the free movement of other cations from the catholyte solution in the membrane.

In this case the cation selective membrane may be positioned on the cathode side of the bimembrane and the anion selective membrane may be positioned on the anode side of the bimembrane. In this case, the cation selective membrane is adapted to allow protons to pass through the membrane from the anode side to the cathode side thereof in operation of the cell. The anion selective membrane is adapted substantially to prevent cationic materials other than protons from passing therethrough from the cathode side to the anode side thereof. In this case protons may pass from anode to cathode.

In a second embodiment of the invention the cation selective membrane is positioned on the anode side of the bimembrane and the anion selective membrane is positioned on the cathode side of the bi-membrane. In this case, the cation selective membrane is adapted to allow protons to pass through the membrane from the anode side to the cathode side thereof in operation of the cell. In this case, anions can pass from the cathode side into the interstitial space of the bimembrane, and protons will pass from the anode side. It may be desirable in this case to provide means for flushing such protons and anionic materials from the interstitial space of the bimembrane. Such means may comprise one or more perforations in the cation selective membrane, allowing such flushing directly through the membrane. Alternatively means may be provided for channelling flushed materials around the cation selective membrane from the interstitial space to the cathode side of the said membrane.

A representative example of a useful bipolar membrane, the arrangement used with the anionic-selective membrane on the anode side is that sold under the trademark Neosepta (R) BP-1, available from Tokuyama Corporation.

According to another aspect of the present invention, there is provided a method of operating a proton exchange membrane fuel cell comprising the steps of:
a) forming H$^+$ ions at an anode situated adjacent to a proton exchange membrane;
b) supplying the catholyte of the invention with its redox mediator in an oxidised state and its redox catalyst in a reduced state to a cathode situated oppositely adjacent to the proton exchange membrane; and
c) allowing the mediator to become reduced upon contact with the cathode concomitantly with H$^+$ ions passing through the membrane to balance charge.

In another embodiment, the catholyte is supplied from a catholyte reservoir.

The method of the above fourth aspect may additionally comprise the step of:
d) passing the catholyte from the cathode to a reoxidation zone wherein the mediator is reoxidised by the catalyst reacting with the oxidant.

In another embodiment, the method of the above aspect comprises the step of:
e) passing the catholyte from the reoxidation zone to the catholyte reservoir.

In this embodiment, the cell is cyclic and the mediator and catalyst in the catholyte can be repeatedly oxidised and reduced without having to be replaced.

An electricity loading device configured to load an electric power may also be provided in association with the fuel cell of the invention.

The fuel cell of the invention may comprise a reformer configured to convert available fuel precursor such as LPG, LNG, gasoline or low molecular weight alcohols into a fuel gas (e.g. hydrogen) through a steam reforming reaction. The cell may then comprise a fuel gas supply device configured to supply the reformed fuel gas to the anode chamber.

Preferred fuels include hydrogen; metal hydrides, for example borohydride which may act as fuel itself or as a provider of hydrogen, low molecular weight alcohols, aldehydes and carboxylic acids, sugars and biofuels as well as LPG, LNG or gasoline.

Preferred oxidants include air, oxygen and peroxides.

The anode in the redox fuel cell of the invention may for example be a hydrogen gas anode or a direct methanol anode; other low molecular weight alcohols such as ethanol, propanol, dipropylene glycol; ethylene glycol; also aldehydes formed from these and acid species such as formic acid, ethanoic acid etc. In addition the anode may be formed from a bio-fuel cell type system where a bacterial species consumes a fuel and either produces a mediator which is oxidized at the electrode, or the bacteria themselves are adsorbed at the electrode and directly donate electrons to the anode.

The cathode in the redox fuel cell of the invention may comprise as cathodic material carbon, gold, platinum, nickel, metal oxide species. However, it is preferable that expensive cathodic materials are avoided, and therefore preferred cathodic materials include carbon, nickel, titanium and other metals inert in the specific catholyte and metal oxide or sulphide. One preferable material for the cathodes is reticulated vitreous carbon or carbon fibre based electrodes such as carbon felt. Another is nickel foam or mesh, or titanium foam or mesh. The cathodic material may be constructed from a fine dispersion of particulate cathodic material, the particulate dispersion being held together by a suitable adhesive, or by a proton conducting polymeric material. The cathode is designed to create maximum flow of catholyte solution to the cathode surface. Thus it may consist of shaped flow regulators or a three dimensional electrode; the liquid flow may be managed in a flow-by arrangement where there is a liquid channel adjacent to the electrode, or in the case of the three dimensional electrode, where the liquid is forced to flow through the electrode. It is intended that the surface of the electrode is also the electrocatalyst, but it may be beneficial to adhere the electrocatalyst in the form of deposited particles on the surface of the electrode.

The redox mediator flowing in solution in the cathode chamber in operation of the cell is used in the invention with a catalyst for the reduction of oxygen in the cathode chamber, in accordance with the following (wherein Sp is the redox couple species).

$$O_2 + 4Sp_{red} + 4H^+ \rightarrow 2H_2O + 4Sp_{ox}$$

The redox couple, and any other ancillary redox couple, utilised in the fuel cell of the invention should be non-volatile, and is preferably soluble in aqueous solvent. Preferred redox couples should react with the oxidant at a rate effective to generate a useful current in the electrical circuit of the fuel cell, and react with the oxidant such that water is the ultimate end product of the reaction.

The fuel cell of the invention requires the presence of at least one redox mediator species and also a redox catalyst comprising a transition metal complex of a multidentate N-donor ligand. However, in some circumstances it may also be possible to include other redox couples in the catholyte solution as ancillary redox couples.

BRIEF DESCRIPTION OF THE DRAWINGS

Various aspects of the present invention will now be more particularly described with reference to the following Figures.

DETAILED DESCRIPTION

Figure 1:
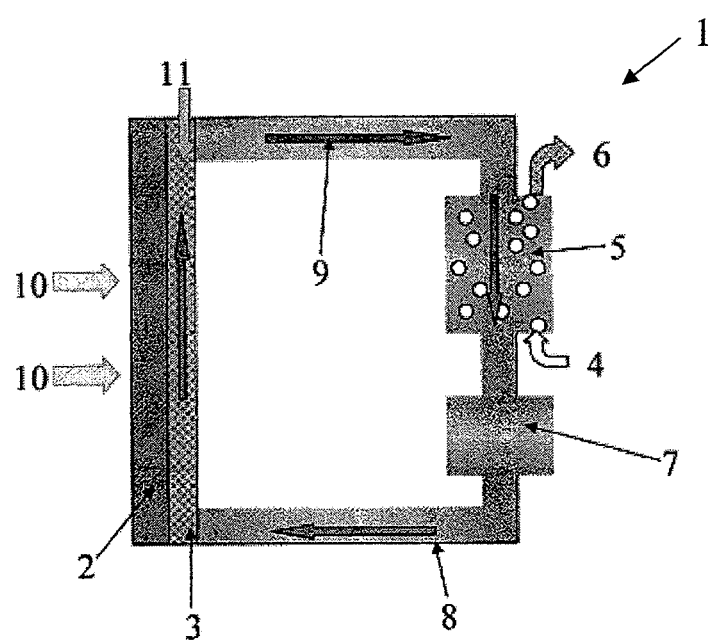
FIG. 1 illustrates a schematic view of the cathode compartment of a fuel cell in accordance with the present invention.

Referring to FIG. 1, there is shown the cathode side of fuel cell 1 in accordance with the invention comprising a polymer electrolyte membrane 2 separating an anode (not shown) from cathode 3. Cathode 3 comprises in this diagram reticulated carbon and is therefore porous. However, other cathodic materials such as platinum may be used. Polymer electrolyte membrane 2 comprises cation selective Nafion 112 membrane through which protons generated by the (optionally catalytic) oxidation of fuel gas (in this case hydrogen) in the anode chamber pass in operation of the cell. Electrons generated at the anode by the oxidation of fuel gas flow in an electrical circuit (not shown) and are returned to cathode 3. Fuel gas (in this case hydrogen) is supplied to the fuel gas passage of the anode chamber (not shown), while the oxidant (in this case air) is supplied to oxidant inlet 4 of cathode gas reaction chamber 5. Cathode gas reaction chamber 5 (the mediator reoxidation zone) is provided with exhaust 6, through which the by-products of the fuel cell reaction (e.g. water and heat) can be discharged.

A catholyte solution comprising the oxidised form of the redox mediator is supplied in operation of the cell from catholyte reservoir 7 into the cathode inlet channel 8. The catholyte passes into reticulated carbon cathode 3, which is situated adjacent membrane 2. As the catholyte passes through cathode 3, the redox mediator is reduced, and is then returned to cathode gas reaction chamber 5 via cathode outlet channel 9.

Due to the advantageous composition of the catholyte of the present invention, reoxidation of the catalyst occurs, catalysed by the transition metal complex of a multidentate N-donor redox catalyst, which allows greater flexibility in designing catholyte systems for the fuel cell to produce for higher potential and/or a higher sustainable current than with catholytes of the prior art.

The following Examples describe the synthesis of a number of multidentate N-donor ligands in accordance with the invention.

EXAMPLE 1

N,N-Bis(pyridine-2-yl-methyl)-bis(pyridine-2-yl) methylamine (N4Py)

(a) Di-2-pyridyl ketone oxime

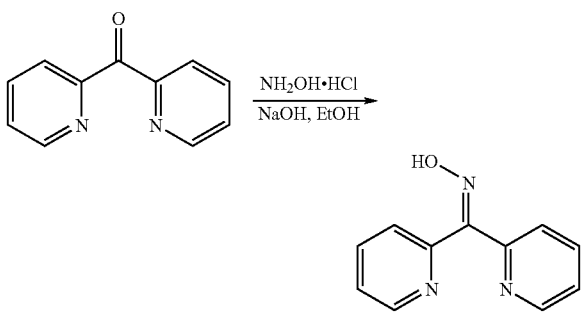

Prepared using the route described by J. Chang et al in *Inorg. Chem.*, 2004, 43, 1735.

(b) Di-2-pyridylmethanamine

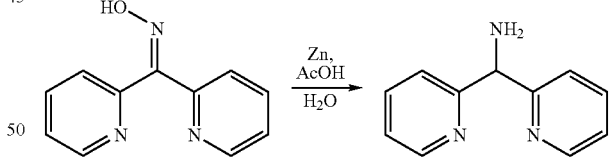

Prepared using the route described by M. van den Heuval et al in *J. Org. Chem.*, 2004, 69, 250.

(c) N,N-Bis(pyridine-2-yl-methyl)-bis(pyridine-2-yl) methylamine

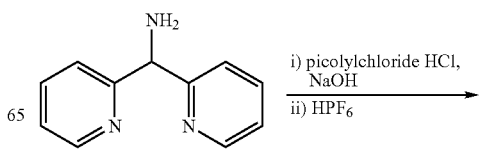

-continued

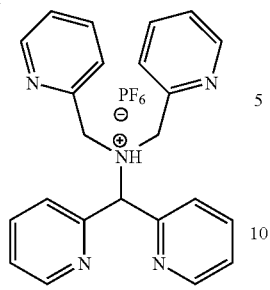

Prepared using a modified version of the route described by M. Lubben et al in *Angew. Chem., Int Ed. Engl.*, 1995, 34, 1512. The only difference being that the hexafluorophosphate salt was isolated instead of the perchlorate salt.

EXAMPLE 2

N,N-Bis(pyridine-2-yl-methyl)-1,1-bis(pyridine-2-yl)-1-amino-ethane (MeN4Py)

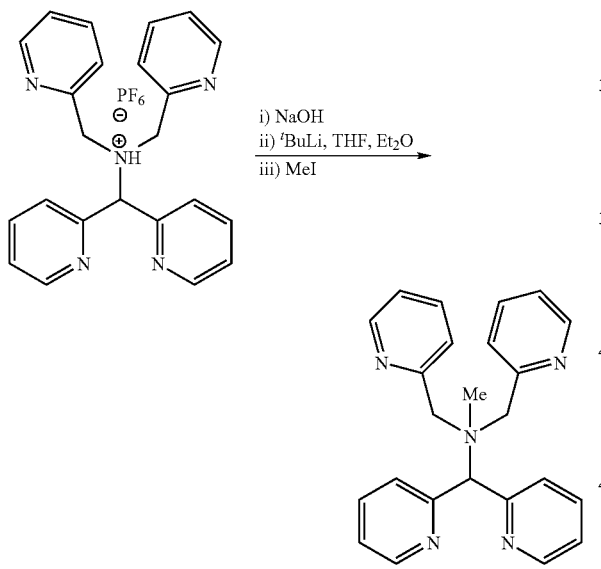

Prepared using the route described by G. Roelfes, PhD Thesis, Rijksuniversiteit Groningen, 2000.

EXAMPLE 3

1,9-Bis(2-pyridyl)-2,5,8-triazanonane trihydrochloride (pydien)

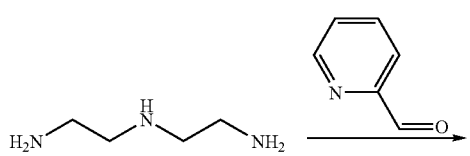

-continued

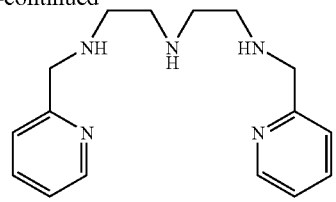

Prepared from diethylenetriamine and pyridine-2-carboxaldehyde using the procedure described by W. R. Harris et al in *Inorg. Chem.*, 1978, 17, 889.

EXAMPLE 4

N-Methyl-N,N',N'-tris(2-pyridylmethyl)ethane-1,2-diamine (trilen)

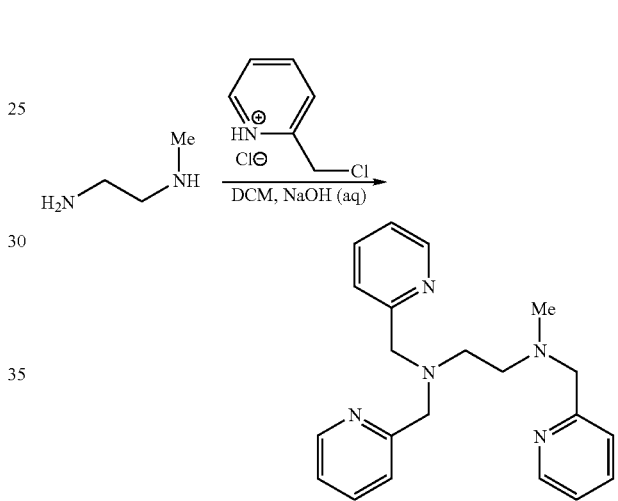

Prepared from N-methylethane-1,2-diamine and 2-chloromethylpyridine hydrochloride using the procedure described by I. Bernal et al in *J. Chem. Soc., Dalton. Trans.*, 1995, 3667.

EXAMPLE 5

N-Methyl-N,N',N'-tris(2-(4-chloro)-pyridylmethyl)ethane-1,2-diamine (trilen-Cl$_3$)

(a) Synthesis of (4-chloro-2-pyridyl)methyl chloride

Prepared using the route described by M. Tamura et al in *Chem. Pharm. Bull.*, 2000, 48, 1514.

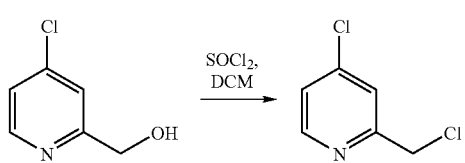

A solution of thionyl chloride (4.47 g, 37.6 mmol) in dichloromethane (70 mL) was added dropwise to a solution of 4-chloro-2-pyridinemethanol (3.0 g, 20.9 mmol) in dichloromethane (80 mL) at reflux. After complete addition, the mixture was heated at reflux for a further 2 hours. The solvent was evaporated, and the residue basified with aqueous Na$_2$CO$_3$ solution (100 mL of 2 M solution). The product was extracted into dichloromethane (3×100 mL) and the combined organic phases were dried over K$_2$CO$_3$. Filtration and evaporation of solvent gave the desired product as a yellow oil (3.19 g, 94%). $^1$H NMR (CDCl$_3$, 500 MHz): δ 4.65 (s, 2H, CH$_2$), 7.26 (d, 1H, Py), 7.48 (d, 1H, Py), 8.45 (d, 1H, Py).

(b) Synthesis of N-methyl-N,N',N',-tris(2-(4-chloro)-pyridylmethyl)ethane-1,2-diamine (trilen-Cl$_3$)

Prepared using a modified version of the route described by M. Tamura et al in *Chem. Pharm. Bull.*, 2000, 48, 1514 for the synthesis of the tetrakis derivative.

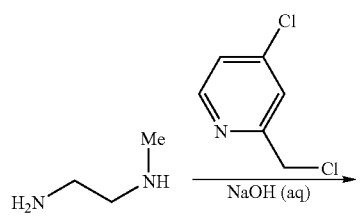

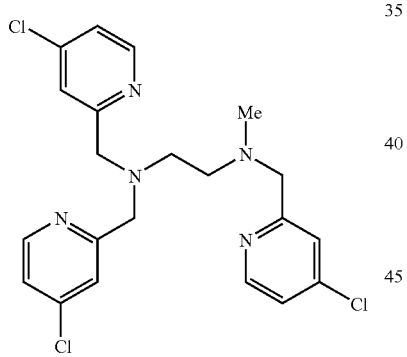

To a suspension of (4-chloro-2-pyridyl)methyl chloride (1.02 g, 6.3 mmol) in water (2.0 mL) was added N-methyl-ethylenediamine (0.148 g, 2.0 mmol), 5.0 M aqueous NaOH solution (2.0 mL) and hexadecyltrimethylammonium chloride (0.06 mL of 25% aqueous solution). The mixture was stirred at room temperature for 72 hours. Water (10 mL) and dichloromethane (20 mL) were added and the product extracted into dichloromethane (3×20 mL). After washing the combined organic phases with water, the solution was dried over MgSO$_4$, filtered and evaporated to dryness to yield a yellow-brown oil (0.88 g, 98%). $^1$H NMR (CDCl$_3$, 500 MHz): δ 2.15 (s, 3H, CH$_3$), 2.58 (t, 2H, CH$_2$CH$_2$), 2.70 (t, 2H, CH$_2$CH$_2$), 3.56 (s, 2H, CH$_2$Ar), 3.78 (s, 4H, CH$_2$Ar), 7.09 (d, 3H, Py), 7.39 (s, 1H, Py), 7.47 (s, 2H, Py), 8.34 (d, 3H, Py).

EXAMPLE 6

N,N,N',N'-Tetrakis(2-pyridylmethyl)ethane-1,2-diamine (tpen)

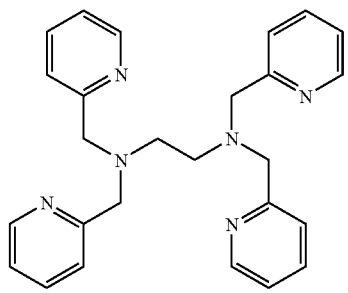 [SMILES: c1ccc(CN(CCN(Cc2ccccn2)Cc2ccccn2)Cc2ccccn2)nc1]

N,N,N',N'-Tetrakis(2-pyridylmethyl)ethane-1,2-diamine was purchased from ABCR GmbH & Co.

EXAMPLE 7

N,N,N',N'-Tetrakis(2-(4-chloro)-pyridylmethyl)ethane-1,2-diamine (tpen-Cl$_4$)

(a) (4-Chloro-2-pyridyl)methyl chloride

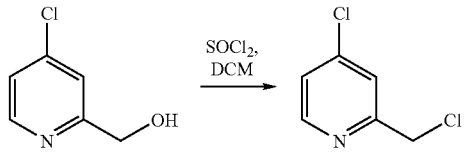 [SMILES: OCc1cc(Cl)ccn1 ; ClCc1cc(Cl)ccn1]

Prepared using the route described by M. Tamura et al in *Chem. Pharm. Bull.*, 2000, 48, 1514.

(b) N,N,N',N'-Tetrakis(2-(4-chloro)-pyridylmethyl)ethane-1,2-diamine

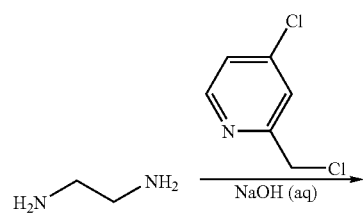

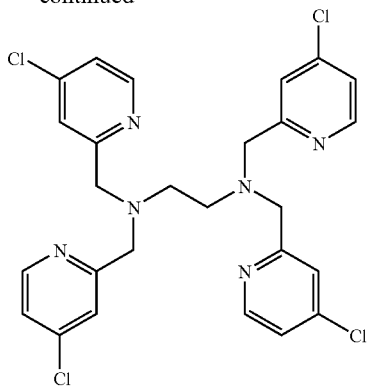

Prepared using the route described by H. Sato et al in *Synthesis*, 1992, 539 and M. Tamura et al in *Chem. Pharm. Bull.*, 2000, 48, 1514.

The performance of the catholyte of the present invention is described in the following Examples.

In the following examples, the oxidation of mediator (dimethylaminomethyl)-ferrocene (Fc-CH$_2$NMe$_2$) by oxygen (Scheme II) was studied at 55-65° C. in 0.1M glycine buffer solution at pH 2.5 in order to evaluate the use of transition metal complexes of N-donor ligands as oxygen reduction catalysts.

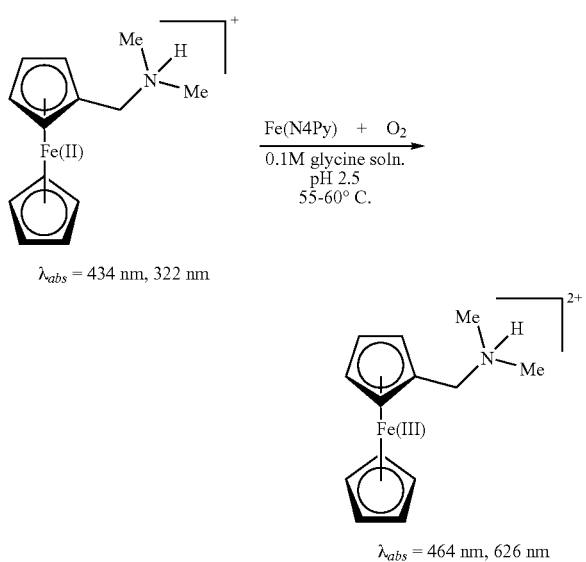

The oxidation of Fc-CH$_2$NMe$_2$ to [Fc-CH$_2$NMe$_2$]$^+$ can be monitored using UV-Vis absorption spectroscopy as the oxidised product exhibits a peak at 626 nm which is not present in any of the starting materials.

The redox potentials of a selection of iron based N-donor complexes for used in these examples were investigated. A standard three electrode cell was used, having (a) a 0.5 cm$^2$ glassy carbon electrode, (b) a reference calomel electrode (SCE) with a luggin capillary placed with the end about 2 mm away from the electrode, and (c) a platinum counter electrode. Cyclic voltammograms were recorded at 50 mV/s at room temperature. All solutions tested contained 1.0 mM of iron complex in 0.1 M glycine solution at pH 2.5, except for Fe(N4Py) which was studied in aqueous solution.

The redox potentials measured for the Fe(II)/(III) couple for a non-limiting selection of N-donor catalysts are given in the table below:

| Catalyst | Potential vs NHE/V |
| --- | --- |
| Fe(N4Py) | 0.608 |
| Fe(MeN4Py) | 0.615 |
| Fe(trilen) | 0.689 |
| Fe(trilen-Cl$_3$) | 0.757 |
| Fe(tpen) | 0.819 |
| Fe(tpen-Cl$_4$) | 0.907 |

EXAMPLE 8

Fe(N4Py)

Experiments were carried out using varying concentrations (0.3 mM and 1.0 mM) of Fe(N4Py) catalyst, generated in situ by combining 0.1M glycine solutions of FeSO$_4$.7H$_2$O and [N4Py-H]$^+$[PF$_6$]$^-$ at pH 2.5.

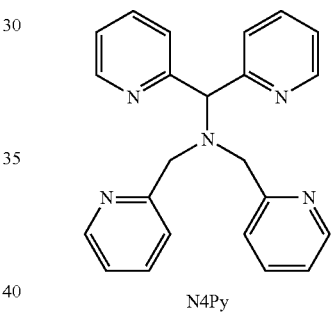

N4Py

The uncatalysed oxidation experiment was also performed under the same conditions as a control experiment. Oxygen was bubbled through 100 mL of solution containing 15 mM Fc-CH$_2$NMe$_2$ and samples were removed at regular time intervals (measured in minutes) in order to record UV-Vis absorption profiles.

Figure 2:
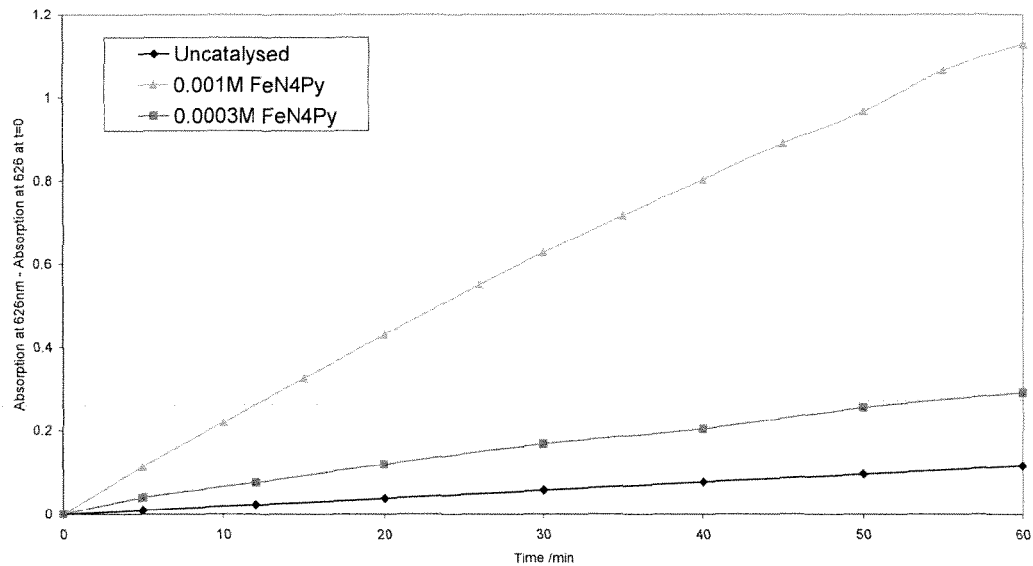
FIG. 2 shows a comparison of the catalysed and uncatalysed rates of oxidation of Fc-CH$_2$NMe$_2$.

A plot of the change in absorbance at 626 nm versus time provides a representation of the relative rates of oxidation of the ferrocene mediator in the presence of either no catalyst, 0.3 mM FeN4Py catalyst or 1.0 mM Fe(N4Py) catalyst. This is shown in FIG. 2 and indicates that catalysis is occurring in the presence of Fe(N4Py), the effect of which is increased upon increasing concentration of catalyst. This data is summarised in Table 1.

EXAMPLE 9

Fe(MeN4Py)

A comparable experiment to that described in Example 8 was conducted using 1.0 mM of Fe(MeN4Py) as the catalyst rather than Fe(N4Py).

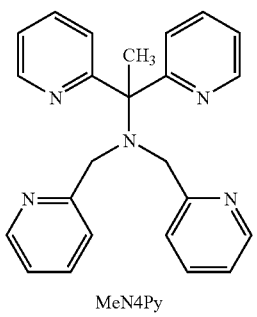 [SMILES: CC(c1ccccn1)(c1ccccn1)N(Cc1ccccn1)Cc1ccccn1]

MeN4Py

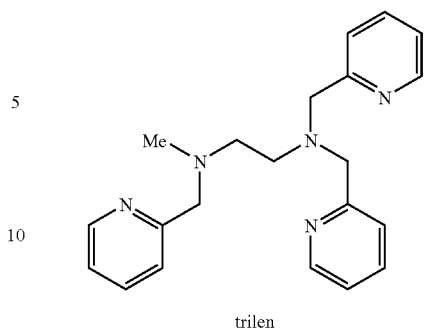

trilen

Figure 3:
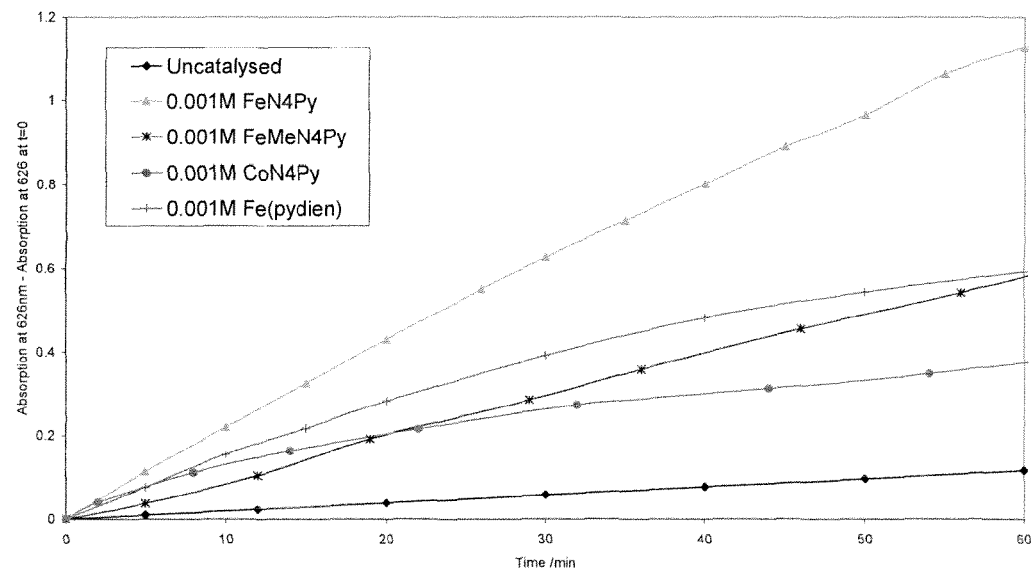
FIG. 3 shows a comparison of the catalysed and uncatalysed rates of oxidation of Fc-CH$_2$NMe$_2$.

Data for this experiment is presented in FIG. 3 and Table 1 and shows that Fe(MeN4Py) is successful as a catalyst for the oxidation of this mediator.

EXAMPLE 10

Co(N4Py)

A 1.0 mM solution of Co(N4Py) was created in situ via the addition of Co(NO$_3$)$_2$ to a solution of [N4Py-H]$^+$[PF$_6$]$^-$ in 0.1M glycine at pH 2.5. This was combined with Fc-CH$_2$NMe$_2$ and the reaction with O$_2$ was studied at ~65° C. over time via UV-Vis spectroscopy. Data is presented in FIG. 3 and shows that Co(N4Py) does act as a catalyst for this oxidation.

EXAMPLE 11

Fe(pydien)

An alternative pentadentate N-donor ligand, 1,9-bis(2-pyridyl)-2,5,8-triazanonane (pydien) (below), was complexed to iron(II) and tested as an oxygen reduction catalyst.

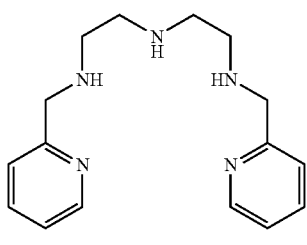

pydien

A 1.0 mM solution of Fe(pydien) was created in situ via the addition of FeSO$_4$.7H$_2$O to a solution of pydien in 0.1M glycine at pH 2.5. This was combined with Fc-CH$_2$NMe$_2$ and the reaction with O$_2$ was studied at 55-60° C. over time via UV-Vis spectroscopy. Data is presented in FIG. 3 and Table 1 and shows that Fe(pydien) does act as a catalyst for this oxidation.

EXAMPLE 12

Fe(trilen)

An alternative pentadentate N-donor ligand, N-methyl-N,N',N'-tris(2-pyridylmethyl)ethane-1,2-diamine (trilen) (below), was complexed to iron(II) and tested as an oxygen reduction catalyst.

Figure 4:
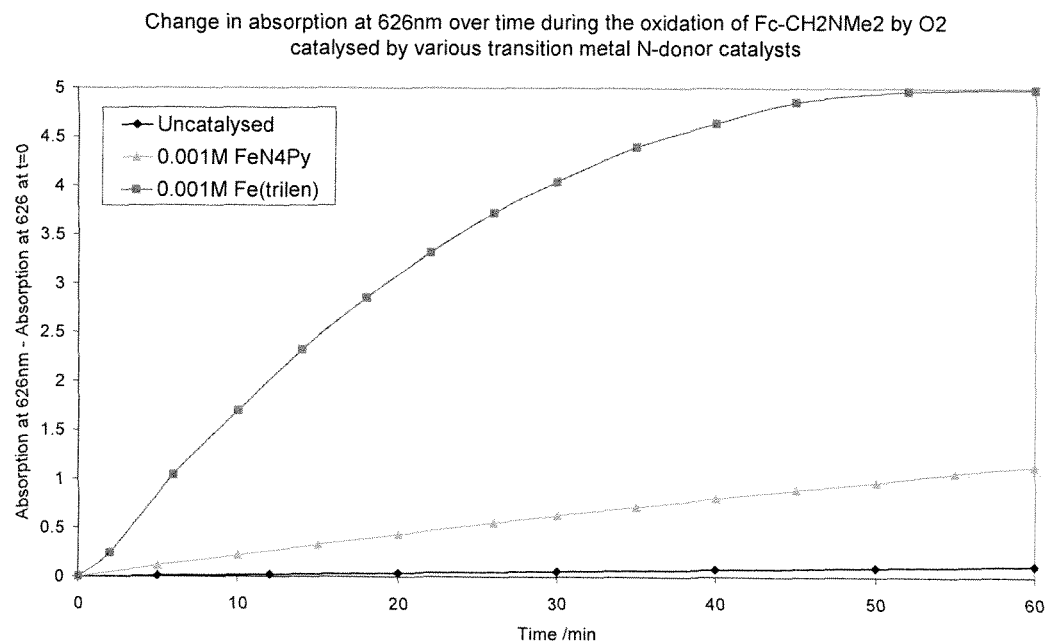
FIG. 4 a comparison of the catalysed and uncatalysed rates of oxidation of Fc-CH$_2$NMe$_2$.

A 1.0 mM solution of Fe(trilen) catalyst was generated in situ via the addition of FeSO$_4$.7H$_2$O to a solution of trilen in 0.1M glycine at pH 2.5. This was combined with Fc-CH$_2$NMe$_2$ and the reaction with O$_2$ was studied at 60° C. over time via UV-Vis spectroscopy. Data is presented in FIG. 4 and Table 1 and shows that Fe(trilen) acts as an efficient catalyst for this oxidation.

EXAMPLE 13

Fe(trilen-Cl$_3$)

An iron complex of a chloro-substituted derivative of trilen (trilen-Cl$_3$, below) was tested as an N-donor catalyst for the oxidation of (dimethylaminomethyl)ferrocene.

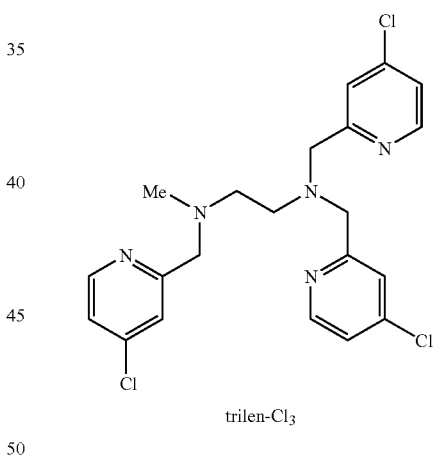

trilen-Cl$_3$

Figure 5:
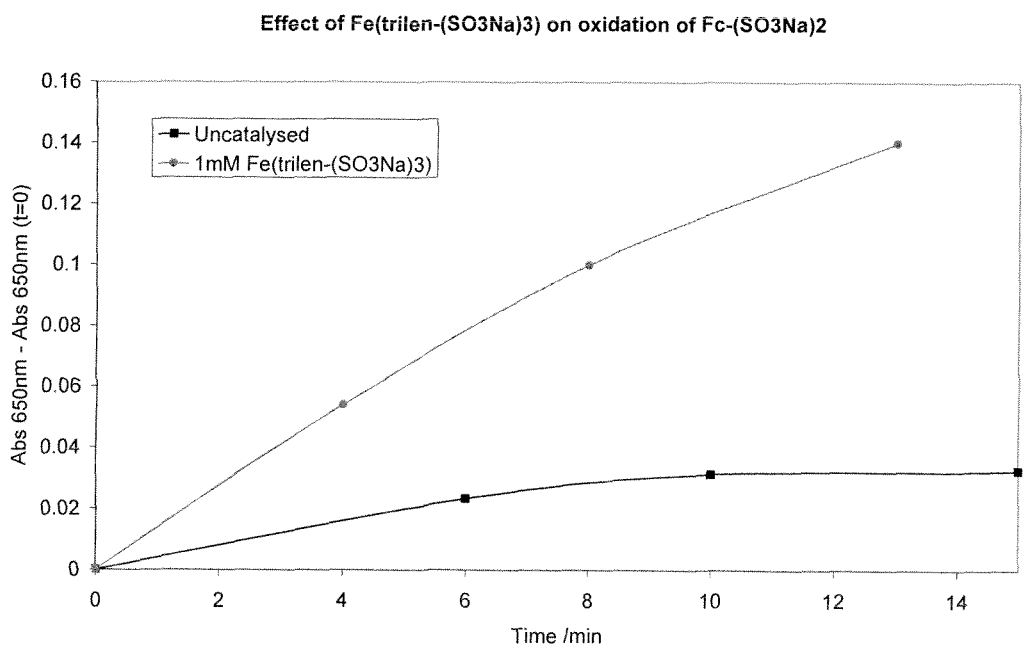
FIG. 5 shows Fe(trilen-(SO$_3$Na)$_3$) acting as a catalyst for the oxidation of 1,1'-bis(methylsulfonato)ferrocene disodium salt.

A 1.0 mM solution of Fe(trilen-Cl$_3$) was generated in situ via the addition of FeSO$_4$.7H$_2$O to a solution of trilen-Cl$_3$ in 0.1M glycine at pH 2.5. This was combined with Fc-CH$_2$NMe$_2$ and the reaction with O$_2$ was studied at 60-65° C. over time via UV-Vis spectroscopy. The data presented Table 1 and FIG. 5 shows that Fe(trilen-Cl$_3$) does act as a catalyst for this oxidation.

EXAMPLE 14

Fe(tpen)

A hexadentate N-donor ligand, N,N,N',N'-tetrakis(2-pyridylmethyl)-ethane-1,2-diamine (tpen) (below) was complexed to iron(II) and tested as an oxygen reduction catalyst.

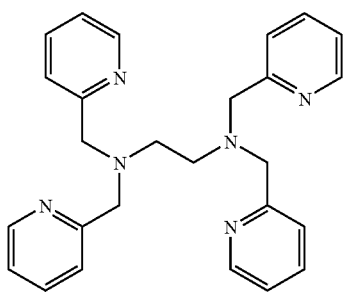 [SMILES: c1ccc(CN(CCN(Cc2ccccn2)Cc2ccccn2)Cc2ccccn2)nc1]

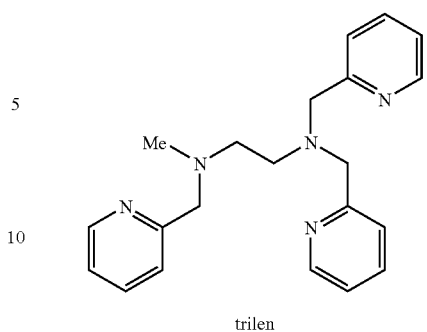

trilen

A 1.0 mM solution of Fe(tpen) was created in situ via the addition of FeSO$_4$.7H$_2$O to a solution of tpen in 0.1M glycine at pH 2.5. This was combined with Fc-CH$_2$NMe$_2$ and the reaction with O$_2$ was studied at 60-65° C. over time via UV-Vis spectroscopy. The data presented Table 1 shows that Fe(tpen) does act as a catalyst for this oxidation.

TABLE 1

| Catalyst | Concentration of Catalyst | Initial Rate of Mediator Oxidation/x$10^{-6}$ Ms$^{-1}$ |
|---|---|---|
| None | — | 0.13 |
| Fe(N4Py) | 1.0 mM | 1.4 |
| Fe(MeN4Py) | 1.0 mM | 0.68 |
| Fe(pydien) | 1.0 mM | 0.94 |
| Fe(trilen) | 1.0 mM | 11.3 |
| Fe(trilen-Cl$_3$) | 1.0 mM | 1.5 |
| Fe(tpen) | 1.0 mM | 1.4 |

The performance of the catholyte of the present invention is also described in the following example, where the N-donor catalyst is used to catalyse the oxidation of a different mediator to that mentioned in the previous examples.

EXAMPLE 15

A catalytic experiment was conducted to monitor the ability of the N-donor catalyst Fe(trilen) to bring about the oxidation of 1,1'-bis(methylsulphonic acid)ferrocene, by oxygen. 1,1'-bis(methylsulphonic acid)ferrocene is a novel material described in our co-pending application PCT/GB2007/050420 (claiming priority from GB 0614338.2) and was synthesised from 1,1'-Bis(chloromethyl)ferrocene in accordance with the following reaction scheme:

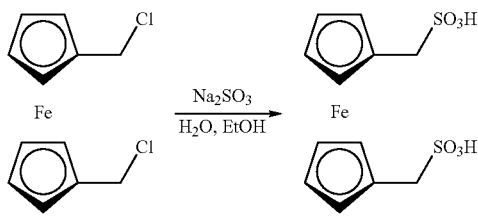

The experiment was conducted at ~65° C. in an aqueous solution containing 0.05 M Na$_2$SO$_4$ and 0.05 M NaHSO$_4$ adjusted to pH 2.5.

A solution containing 1.0 mM of Fe(trilen) catalyst was generated in situ by combining solutions of FeSO$_4$.7H$_2$O and trilen.

An uncatalysed oxidation experiment was also performed under the same conditions as a control experiment. Oxygen was bubbled through 25 mL of solution containing approximately 10 mM 1,1'-bis(methylsulphonic acid)-ferrocene and samples were removed at regular time intervals (measured in minutes) in order to monitor the production of the oxidised ferrocene species via the UV-Vis absorption peak at 650 nm. This data is summarised in Table 2 and shows that Fe(trilen) acts as an efficient catalyst for the oxidation of 1,1'-bis(methylsulphonic acid)-ferrocene.

TABLE 2

| Experiment | Uncatalysed | 1.0 mM Fe(trilen) |
|---|---|---|
| Change in absorption at 650 nm after 3 minutes | 0.003 | 0.270 |

EXAMPLE 16

A catalytic experiment was conducted to monitor the ability of the iron complex of N-donor ligand N-methyl-N,N',N',-tris(2-(4-sulfonato)-pyridylmethyl)ethane-1,2-diamine trisodium salt (Fe(trilen-(SO$_3$Na)$_3$)) to bring about the oxidation of 1,1'-bis(methylsulfonato)ferrocene disodium salt, by oxygen.

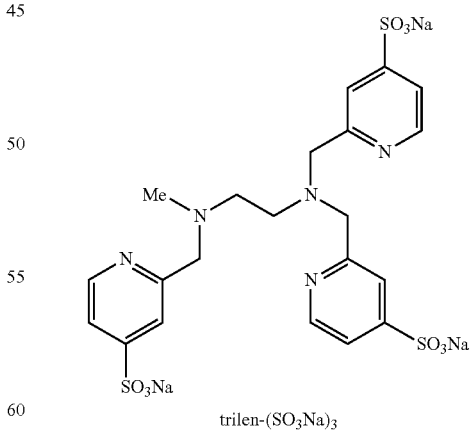

trilen-(SO$_3$Na)$_3$

The N-donor ligand N-methyl-N,N',N',-tris(2-(4-chloro)-pyridylmethyl)ethane-1,2-diamine (trilen-Cl$_3$) was reacted with Na$_2$SO$_3$ in an ethanol/water mixture to produce the N-donor species N-methyl-N,N',N',-tris(2-(4-sulfonato)-pyridylmethyl)ethane-1,2-diamine trisodium salt (trilen- (SO$_3$Na)$_3$). NMR data, after several days of heating at reflux, was consistent with sulfonated product.

To test as an N-donor catalyst for the reduction of oxygen, an excess of this ligand was combined with a measured amount of Fe(II) to generate a known concentration of Fe(trilen-(SO$_3$Na)$_3$) catalyst.

A catalytic experiment was conducted using a solution containing 1.0 mM of the iron(II) complex of this sulfonated N-donor, 10 mM of mediator species 1,1'-bis(methylsulfoato)ferrocene disodium salt [Fc-(CH$_2$SO$_3$Na)$_2$] and 0.1 M glycine buffer at pH 2.5. The solution was heated to 65° C. and bubbled with oxygen. The reaction was monitored by UV-Vis absorption spectroscopy to measure the increase in absorption at 650 nm. An uncatalysed oxidation experiment was also performed under the same conditions as a control experiment. This data is summarised in FIG. 5 and shows that Fe(trilen-(SO$_3$Na)$_3$) acts as a catalyst for the oxidation of 1,1'-bis(methylsulfonato)ferrocene disodium salt.

EXAMPLE 17

A catholyte solution of the present invention was prepared and its performance assessed using a redox cathode and a hydrogen anode. A commercial anode was used with a platinised gas diffusion layer from E-TEK (De Nora Deutschland), ½ MEA from Ion Power Inc using a 0.125 mm Nafion® (DuPont) membrane. A reticulated vitreous carbon (RVC) electrode was used for the cathode. The catholyte solution was pumped through this electrode before passing to a reservoir from where it was recirculated. The total liquid volume was 25 cm$^3$.

Figure 6:
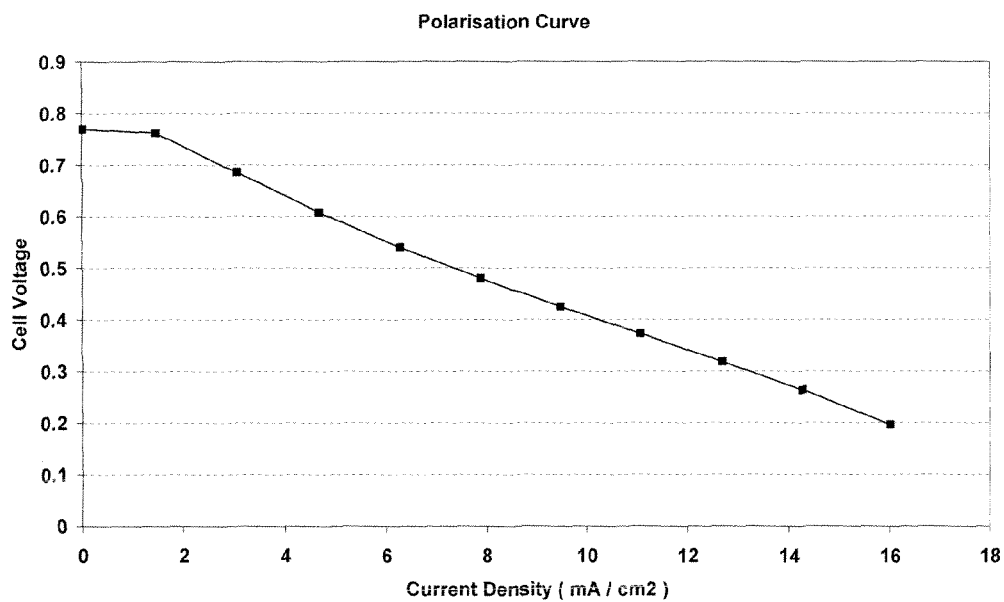
FIG. 6 shows a polarisation curve in a fuel cell according to the invention.

The catholyte solution tested contained 10 mM 1,1'-bis (methylsulfonato)-ferrocene disodium salt and 1.0 mM Fe(trilen-(SO$_3$Na)$_3$) in a buffer solution containing 0.05 M Na$_2$SO$_4$ and 005M NaHSO$_4$ at pH 2. The catholyte was partially oxidised by bubbling oxygen through the solution at 65° C. for 30 minutes whereupon the absorbance at 650 nm was measured as 0.24. This resulting solution was flowed through the fuel cell whilst a polarisation curve was recorded. This can be seen in FIG. 6.

Figure 7:
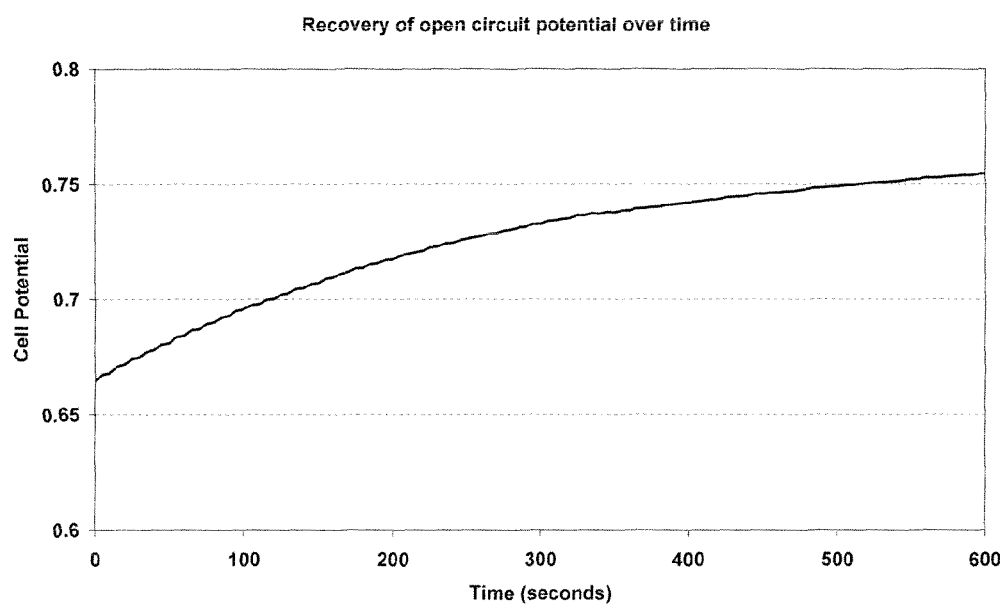
FIG. 7 shows the ability of a catholyte in accordance with the invention to regenerate, assessed by monitoring the recovery of the open circuit potential of the cell whilst bubbling oxygen through the catholyte.

The solution was partially reduced in the fuel cell by drawing a current over a period of several minutes. The ability of the catholyte to regenerate was then assessed by monitoring the recovery of the open circuit potential whilst bubbling oxygen through the catholyte. This data can be seen in FIG. 7.

The invention claimed is:

1. A redox fuel cell comprising:
an anode region comprising an anode and a cathode region comprising a cathode, said regions being separated by an ion selective polymer electrolyte membrane;
a fuel passage through which fuel is supplied to the anode region of the cell;
an oxidant inlet that supplies an oxidant to the cathode region of the cell;
an electrical circuit between the anode and the cathode; and
a catholyte solution comprising at least one non-volatile catholyte component flowing in fluid communication with the cathode, the catholyte solution comprising a redox mediator and a separate redox catalyst, wherein the redox mediator is at least partially reduced at the cathode in operation of the cell, and at least partially regenerated by reaction with the oxidant after such reduction at the cathode;
wherein the catholyte solution comprises a complexed multidentate N-donor ligand as the redox catalyst.

2. A fuel cell according to claim 1 wherein the catholyte solution comprises a material which is not the complexed multi-dentate N-donor ligand as the redox mediator and the complexed multidentate N-donor ligand as the redox catalyst for the redox mediator.

3. A fuel cell according to claim 1 wherein the catholyte solution comprises the complexed multidentate N-donor ligand as the redox mediator and a further material which is not the complexed multi-dentate N-donor ligand as the redox catalyst for the ligand complex redox mediator.

4. A fuel cell according to claim 1 wherein in operation of the cell, the oxidant is reduced in the catholyte solution by the redox catalyst.

5. A fuel cell according to claim 4 wherein the redox catalyst, after reduction of the oxidant in the catholyte solution, is effective to at least partially oxidize the mediator to regenerate the redox mediator after its reduction at the cathode.

6. A fuel cell according claim 1 wherein the catholyte solution is an aqueous solution.

7. A fuel cell according to claim 1 wherein the complexed multidentate N-donor ligand comprises a transition metal complex of the multidentate N-donor ligand.

8. A fuel cell according to claim 7 wherein the multidentate N-donor ligand comprises at least one pyridine substituent.

9. A fuel cell according to claim 8 wherein the multidentate N-donor ligand comprises at least two pyridine substituents.

10. A fuel cell according to claim 9 wherein the multidentate ligand is complexed to a transition metal via 3 to 6 nitrogen atoms.

11. A fuel cell according to claim 10 wherein one to five of said nitrogen atoms are contained in one or more aromatic heterocycles.

12. A fuel cell according to claim 11, wherein the aromatic heterocycles are substituted aromatic heterocycles.

13. A fuel cell according claim 1 wherein the N-donor ligand has the structure:

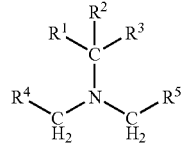

wherein R$^1$-R$^5$ comprise two to five organic groups which each include at least one N donor atom.

14. A fuel cell according to claim 13 wherein said organic groups which include at least one N donor atom are aromatic heterocycles.

15. A fuel cell according to claim 14 wherein said aromatic heterocycles comprise pyridine or pyridine derivatives.

16. A fuel cell according to claim 14, wherein the aromatic heterocycles are substituted aromatic heterocycles.

17. A fuel cell according to claim 1 wherein the multidentate N-donor ligand has the structure:

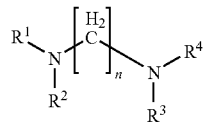

wherein n is an integer selected between 1 and 10 and R$^1$-R$^4$ comprise 1 to 4 organic groups which each include at least one N donor atom.

18. A fuel cell according to claim 17 wherein said organic groups which include at least one N donor atom are aromatic heterocycles.

19. A fuel cell according to claim 18 wherein said aromatic heterocycles comprise pyridine or pyridine derivatives.

20. A fuel cell according to claim 18, wherein the aromatic heterocycles are substituted aromatic heterocycles.

21. A fuel cell according to claim 1 wherein the multidentate N-donor ligand has the structure:

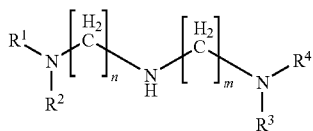

wherein n and m are each integers selected between 1 and 10 and wherein $R^1$ to $R^4$ comprise one to three organic groups which each include at least one N donor atom.

22. A fuel cell according to claim 21 wherein said organic groups which include at least one N donor atom are aromatic heterocycles.

23. A fuel cell according to claim 22 wherein said aromatic heterocycles comprise pyridine or pyridine derivatives.

24. A fuel cell according to claim 22, wherein the aromatic heterocycles are substituted aromatic heterocycles.

25. A fuel cell according to claim 1 wherein the multidentate N-donor ligand is selected from the group consisting of N4Py (N,N-bis(pyridine-2-yl-methyl)-bis(pyridine-2-yl)methylamine) and derivatives thereof, pydien (1,9-bis(2-pyridyl)-2,5,8-triazanonane) and derivatives thereof, trilen (N-methyl-N,N',N'-tris(2-pyridylmethyl)ethane-1,2-diamine) and derivatives thereof.

26. A fuel cell according to claim 1 wherein the ion selective polymer electrolyte membrane is a cation selective membrane which is selective in favor of protons versus other cations.

27. A fuel cell according to claim 26 wherein the catholyte is acidic.

28. A fuel cell according to claim 1 wherein the ion selective polymer electrolyte membrane is an anion selective membrane.

29. A fuel cell according to claim 28 wherein the catholyte is alkaline.

30. A fuel cell according to claim 1 wherein the ion selective polymer electrolyte membrane is a bimembrane.

31. A fuel cell according to claim 1 wherein the redox mediator comprises a modified ferrocene species.

32. The fuel cell of claim 1, wherein the redox mediator is at least partially regenerated by indirect reaction with the oxidant after reduction at the cathode.

* * * * *